US012594412B2

(12) United States Patent (10) Patent No.: US 12,594,412 B2
Yee et al. (45) Date of Patent: Apr. 7, 2026

(54) FLUSH SYRINGE WITH MULTIPLE SCRUBBING DEVICES

(71) Applicant: Becton, Dickinson and Company, Franklin Lakes, NJ (US)

(72) Inventors: Alban Yee, Waldwick, NJ (US); Shishir Prasad, Ramsey, NJ (US); Manish Kumar, Bengaluru (IN); Narasinha C. Parasnis, Nanuet, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 675 days.

(21) Appl. No.: 18/047,735

(22) Filed: Oct. 19, 2022

(65) Prior Publication Data

US 2024/0131317 A1 Apr. 25, 2024
US 2024/0226528 A9 Jul. 11, 2024

(51) Int. Cl.
A61M 39/16 (2006.01)
A61M 39/10 (2006.01)
A61M 39/20 (2006.01)

(52) U.S. Cl.
CPC ............ A61M 39/16 (2013.01); A61M 39/20 (2013.01); A61M 2039/1033 (2013.01)

(58) Field of Classification Search
CPC .. A61M 39/162; A61M 39/165; A61M 39/16; A61M 39/20
See application file for complete search history.

(56) References Cited

U.S. PATENT DOCUMENTS 7,780,794 B2    8/2010  Rogers et al.
8,167,847 B2    5/2012  Anderson et al.
(Continued)

FOREIGN PATENT DOCUMENTS

AU        2015353815 B2    12/2020
CA          2675708 A1     7/2008
(Continued)

OTHER PUBLICATIONS

PCT International Search Report and Written Opinion in PCT/US2023/035467 dated Feb. 12, 2024, 15 pages.

*Primary Examiner* — Bradley J Osinski
(74) *Attorney, Agent, or Firm* — Servilla Whitney LLC

(57) ABSTRACT

An integrated disinfection device is described syringe assembly having two integrated disinfection units assembled to a syringe for disinfecting and sterilizing corresponding medical connectors, specifically access ports of corresponding medical connectors. The integrated disinfection unit includes a first cup and a second cup. The first cup having a chamber containing a first absorbent material, a first disinfectant or an antimicrobial agent in the first cup, and a first peelable seal. The second cup having a chamber containing a second absorbent material, a second disinfectant or an antimicrobial agent in the second cup, and a second peelable seal. A threaded connection is disposed on the bottom exterior surface of the first cup having threads that are sized and pitched to engage threads of a luer lock collar on the distal end of the syringe barrel to allow the first cup to be connected to the syringe assembly. The second cup and the syringe assembly are interlocked through interference fit or snap fit of the thumb press of the syringe and ledge of the second cup.

19 Claims, 22 Drawing Sheets

(56) References Cited

U.S. PATENT DOCUMENTS

| | | | |
|---|---|---|---|
| 8,172,825 B2 | 5/2012 | Solomon et al. | |
| 8,177,761 B2 | 5/2012 | Howlett et al. | |
| 8,197,749 B2 | 6/2012 | Howlett et al. | |
| 8,328,767 B2 | 12/2012 | Solomon et al. | |
| 8,419,713 B1 | 4/2013 | Solomon et al. | |
| 8,523,830 B2 | 9/2013 | Solomon et al. | |
| 8,574,490 B2 | 11/2013 | Haytman et al. | |
| 8,647,326 B2 * | 2/2014 | Solomon | A61M 39/162 |
| | | | 604/533 |
| 8,740,864 B2 | 6/2014 | Hoang et al. | |
| 8,779,386 B2 | 7/2014 | Bak | |
| 8,784,388 B2 | 7/2014 | Charles et al. | |
| 8,980,174 B2 | 3/2015 | Haytman et al. | |
| 9,039,989 B2 | 5/2015 | Liu et al. | |
| 9,259,284 B2 | 2/2016 | Rogers et al. | |
| 9,259,535 B2 | 2/2016 | Anderson et al. | |
| 9,283,369 B2 | 3/2016 | Ma et al. | |
| 9,295,742 B2 | 3/2016 | Rasooly et al. | |
| 9,399,125 B2 | 7/2016 | Burkholz | |
| 9,480,833 B2 | 11/2016 | Hoang et al. | |
| 9,592,374 B2 | 3/2017 | Muse | |
| 9,700,710 B2 | 7/2017 | Anderson et al. | |
| 9,867,975 B2 | 1/2018 | Gardner et al. | |
| 9,895,526 B2 | 2/2018 | Korogi et al. | |
| 9,907,617 B2 | 3/2018 | Rogers | |
| 9,956,307 B2 | 5/2018 | Burapachaisri et al. | |
| 10,166,381 B2 | 1/2019 | Gardner et al. | |
| 10,814,025 B2 | 10/2020 | Bonutti et al. | |
| 2011/0054440 A1 | 3/2011 | Lewis | |
| 2015/0374968 A1 | 12/2015 | Solomon et al. | |
| 2016/0325089 A1 | 11/2016 | Burkholz | |
| 2017/0181810 A1 | 6/2017 | Tennican | |
| 2017/0232185 A1 | 8/2017 | Wilson et al. | |
| 2019/0234540 A1 * | 8/2019 | Marici | A61M 39/20 |
| 2020/0121858 A1 * | 4/2020 | Anderson | A61M 5/31511 |
| 2020/0222682 A1 | 7/2020 | Burkholz | |
| 2021/0077805 A1 | 3/2021 | Charles et al. | |
| 2021/0138224 A1 | 5/2021 | Marici | |

FOREIGN PATENT DOCUMENTS

| | | | |
|---|---|---|---|
| CA | 3040277 A1 | 4/2018 |
| CN | 101495167 A | 7/2009 |
| CN | 106861032 A | 6/2017 |
| EP | 2359883 B1 | 5/2013 |
| EP | 3691741 A4 | 7/2021 |
| JP | 2021511132 A | 5/2021 |
| NO | 2017087400 A1 | 5/2017 |
| WO | 2010023329 A1 | 3/2010 |
| WO | 2011066565 A1 | 6/2011 |
| WO | 2011066586 A1 | 6/2011 |
| WO | 2012162259 A2 | 11/2012 |
| WO | 2013184716 A1 | 12/2013 |
| WO | 2014120620 A1 | 8/2014 |
| WO | 2018140284 A1 | 8/2018 |

* cited by examiner

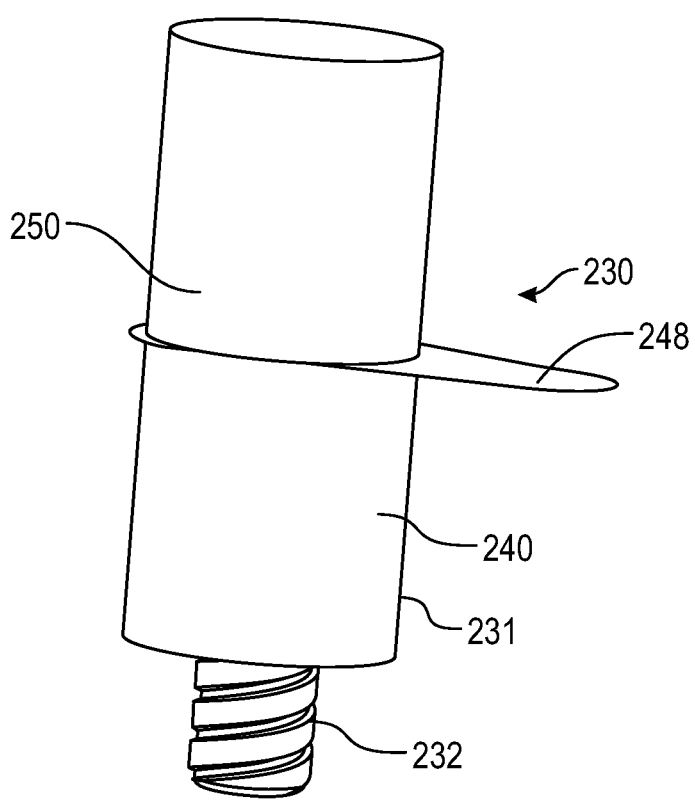
FIG. 10
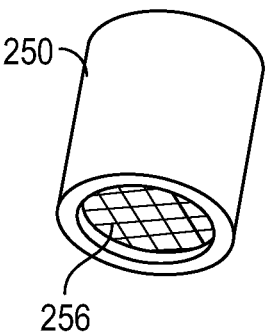
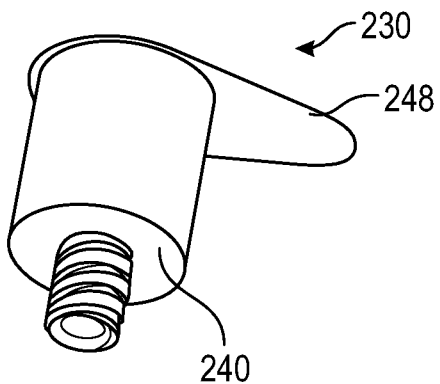
FIG. 11

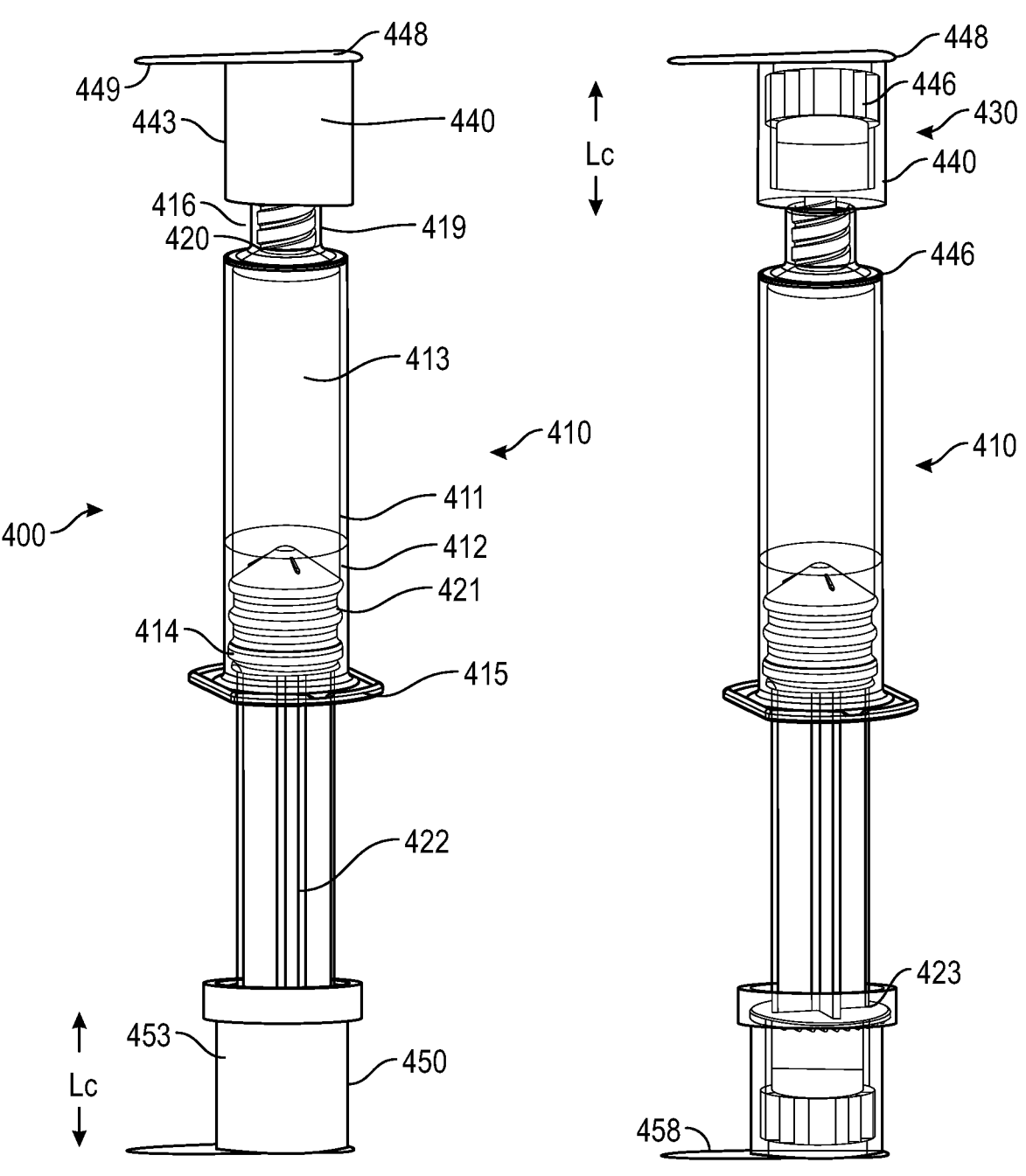
FIG. 19                    FIG. 20

FLUSH SYRINGE WITH MULTIPLE SCRUBBING DEVICES

TECHNICAL FIELD

The present disclosure generally relates to an integrated disinfection unit having a scrubbing device having a first cup and a second cup. The first cup comprises an integral body, a closed end, an annular wall extending from the closed end to an open end that defines a chamber containing a first absorbent material, a first disinfectant, and a first peelable seal. The second cup comprises an integral body, a closed end, an annular wall extending from the closed end to an open end that defines a chamber containing a second absorbent material, a second disinfectant, and a second peelable seal. The present disclosure also generally relates to a syringe assembly having two integrated disinfection units assembled to a syringe for disinfecting and sterilizing corresponding medical connectors, specifically access ports of corresponding medical connectors.

BACKGROUND

Vascular access devices (VADs) are commonly used therapeutic devices, which include intravenous (IV) catheters and needleless access devices. The operation of VADs is often compromised or completely prevented by the occurrence of thrombus formation. Thrombosis is the development of a blood clot within a vessel and/or vascular access device. If not properly maintained or if exposed to a non-sterile environment, the VADs can become contaminated, sealed with blood clots or spread infection. Bacteria and other microorganisms may enter a patient's vascular system from access hub, port, or valve upon connection to the VAD to deliver the fluid or pharmaceutical. Each access hub, port, valve or connection is associated with some risk of transmitting a catheter related bloodstream infection (CRBSI), which can be costly and potentially lethal. In order to decrease CRBSI cases and to ensure VAD's are used and maintained correctly, standards of practice have been developed, which include disinfecting and cleaning procedures. To ensure VADs are used properly and do not become sealed or infected, protocols to ensure sterile practice have been developed. These protocols include sterilizing the VAD and flushing the catheter with a flush solution. Catheters are flushed using syringe assemblies filled with various fluids. In some cases, different fluids are injected sequentially in accordance with the protocol. For example, a saline solution followed by an anticoagulant such as heparin. VAD protocols usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections.

In developed markets, when utilizing an IV catheter, a needleless connector will typically be used to close off the system and then subsequently accessed to administer medication or other necessary fluids via the catheter to the patient. Infusion Nurses Society ("INS") Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. By way of example, contamination can occur during drug mixing, attachment of a cannula, and insertion into the access hub. Furthermore, threaded connectors have an open luer with an exposed lumen. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

VAD standards and practices commonly include disinfecting both the threaded male connector and the IV catheter connection. The additional disinfection steps decrease the likelihood of contamination while also increasing the likelihood of non-compliance with disinfection procedures.

Current "recommended practice" for aseptic IV line maintenance and IV drug delivery practices require adherence to a stepwise process referred to as "SASH." During the first step of the process, the clinician cleans/disinfects (generally with an alcohol swab) the VAD connector. Second, a syringe containing saline is used to flush the IV line or catheter (Saline flush), and then the VAD connector is disinfected a second time. Third, the fluid or pharmaceutical therapy is administered through the IV line or catheter (Administer therapy), the VAD connector is disinfected a third time, followed by a second Saline flush step. The final step, which is dependent upon the patient's need and institutional policy, is a final disinfection of the VAD connector followed by a Heparin lock step, where a small amount of heparin is injected into the IV line or catheter to prevent the formation of thrombi or blood clots. A separate disinfecting cap may be used to sterilize the hub of the VAD. This "recommended practice" requires disinfecting the VAD connector after each access makes IV line maintenance a very burdensome and time consuming process. Because the process is so cumbersome, clinicians are less likely to implement this "recommended practice" in its entirety, and, thus, patients are exposed to the risk of contracting CRBSIs. Microorganisms populate exposed connector inlet surfaces, and, when the "recommended practice" is not adhered to, the microorganisms can enter the IV line during flushing. Furthermore, blood reflux into the IV line or catheter can cause clot formation inside the lines, and microorganisms from the connector inlet surfaces can colonize blood clots inside the lines and infect the patients during flushing.

Current practice requires users to obtain a separate disinfection unit product to ensure the VAD connector cleanliness after, e.g. saline flush and before the next procedure, e.g. medication injection. There is a need, therefore, for an integrated disinfection unit assembled to a syringe that promotes compliance with aseptic technique by eliminating the additional swabbing and disinfecting steps while reducing the number of separate flushing and disinfecting apparatuses used in current practice.

Currently, the workflow to sanitize hub is performed with only one single device, which is typically an IPA pad or similar IPA scrubbing device. After the sanitation is performed, the line is flushed with the syringe. Next, the medication is administered to the patient. The hub sanitization prior to this administration can easily be missed as the IPA pad or scrubbing device is not readily available. Next, a second flush is performed to clear the line. An IPA pad or scrubbing device is used to clean the hub prior to use if it is integrated with the flush syringe. Lastly, the line is locked with a lock solution (example: heparin), but the hub is not sanitized prior to administration as the IPA pad or scrubbing device is not readily available. Currently products and practice does not address any cleaning after flushing as the sanitization ends after the flush. INS guidelines also recommend cleaning the connector before each access. Thus, current solutions on the market do not include additional scrubbing devices to enforce sanitization prior to medication or lock solution administration.

Thus, there is a need to provide a device including two or more IPA pads or scrubbing devices to sanitize the hub or connecting interface prior to medication or lock solution administration.

SUMMARY

One aspect of the present disclosure pertains to a disinfection device for connection to a medical connector. According to an exemplary embodiment of the present disclosure, the disinfection device generally comprises a scrubbing device having a first cup and a second cup and a bottom wall spanning the entirety of the first cup and the second cup.

The first cup comprises an integral body, a closed end, an annular wall having a length $L_C$ extending from the closed end to an open end that defines a chamber containing a first absorbent material, a first disinfectant or an antimicrobial agent, and a first peelable seal having a top web. The first peelable seal has a bottom surface and a top surface.

The second cup comprises an integral body, a closed end, an annular wall having a length LC extending from the closed end to an open end that defines a chamber containing a second absorbent material, the closed end of the annular wall having a ledge extending from the closed end, a second disinfectant or an antimicrobial agent in the second cup, and a second peelable seal having a top web. The second absorbent material is soaked in the second disinfectant or the antimicrobial agent.

The open end of the first cup defines an engagement surface to contact bottom surface of the first peelable seal and the open end of the second cup defines an engagement surface to contact the top surface of the second peelable seal.

A connection element is disposed on the bottom wall of the scrubbing device allowing it to be connected to a syringe. In one or more embodiments, the syringe assembly can be attached to the scrubbing device using various methods including, but not limited to, mechanical fasteners, snap-fittings, and threaded connection. In one or more embodiments, the connection element is a threaded connection and may include integrated threads or tabs. In a specific embodiment, the connection element is a luer threaded connection. In one or more embodiments, a threaded connection is disposed on the bottom exterior surface of the first cup of the disinfection unit having threads that are sized and pitched to engage threads of a luer lock collar on the distal end of the syringe barrel to allow the first cup to be connected to a syringe. In one or more embodiments, the bottom wall of the first cup of the scrubbing device includes a threaded post disposed in the center of the bottom wall of the first cup that corresponds to the internal thread of the locking luer-type collar on the distal end of the syringe barrel.

The second cup and the syringe assembly are interlocked through interference fit or snap fit of the thumb press of the syringe and a ledge of the second cup. A ledge or wedge can be arranged at the closed end of the annular wall of the second cup to provide for a snap fit connection to the thumb press of a syringe assembly. The inner surface of the top wall of the second cup disposed at the closed end of the annular wall of the second cup may have a recess, ledge or wedge into which the thumb press may be inserted.

In one or more embodiments, the closed end of the annular wall of the second cup includes a peripheral sidewall extending radially inward in a perpendicularly direction from the annular wall. The second cup is adapted to be snap fitted over the thumb press of the plunger rod, opposite of a luer tip. In one or more embodiments, the second cup may be connected to the thumb press with a rim disposed on the peripheral ledge and radially inward to create a lip or rim.

In one or more embodiments, an interior surface of the peripheral ledge in the interior annular wall surface of the second cup at the closed end includes at least two or more mating protrusions which allow the thumb press to mate together with the second cup via a snap fit connection.

The scrubbing device can achieve disinfection when used on needle-free connector ("NFC") by integrating a first disinfectant or antimicrobial agent in the first absorbent material disposed and housed in the first chamber of the cup and a second disinfectant or antimicrobial agent in the second absorbent material disposed and housed in the second chamber of the second cup. The first and second disinfectant or antimicrobial agent can be directly included in the first chamber and second chamber and can be absorbed into first absorbent material and into second absorbent material (e.g. sponges or foam material) that fills the chamber of first cup and second cup respectively. The scrubbing device is designed to be compatible in interacting with various disinfectants. In one or more embodiments, the first disinfectant or antimicrobial agent or second disinfectant or antimicrobial agent may include variations of alcohol or chlorhexidine. In one or more embodiments, the first disinfectant or antimicrobial agent or second disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the first disinfectant or antimicrobial agent or second disinfectant or antimicrobial agent comprises at least one of chlorhexidine gluconate and chlorhexidine diacetate. In one or more embodiments, the first disinfectant or antimicrobial agent or second disinfectant or antimicrobial agent is a fluid or a gel.

First absorbent material soaks up the first disinfectant or the antimicrobial agent that is housed within the chamber of the cup. In one or more embodiments, the first absorbent material is a nonwoven material, foam, or a sponge. In a specific embodiment, the foam is a polyurethane foam. In a specific embodiment the first absorbent material is in the form of a foam plug. In one or more embodiments, the first absorbent material includes one or more slits.

A first peelable seal having a top web is disposed on the engagement surface of cup to prevent the first absorbent material from exiting the chamber. With the first absorbent material properly inserted into the chamber of the cup, the first peelable seal may be secured to the engagement surface of the open end of the first cup to seal the scrubbing device.

Second absorbent material is disposed and housed in the chamber of the cup and soaks up the second disinfectant or the antimicrobial agent that is housed within the chamber of the second cup. In one or more embodiments, the second absorbent material is a nonwoven material, foam, or a sponge. In a specific embodiment, the foam is a polyurethane foam. In a specific embodiment the second absorbent material is in the form of a foam plug. In one or more embodiments, the second absorbent material includes one or more slits.

A second peelable seal having a top web is disposed on the engagement surface of cup to prevent the second absorbent material from exiting the chamber. With the second absorbent material properly inserted into the chamber of the cup, the second peelable seal may be secured to the engagement surface of the open end of the second cup to seal the scrubbing device.

The first peelable seal and second peelable seal can be chemically-resistant, light-blocking, non-permeable, or sterile. In one or more embodiments, the first peelable seal and second peelable seal comprises an aluminum or multi-layer polymer film peel back top. In a specific embodiment, the first peelable seal and second peelable seal is heat-sealed or induction sealed to the engagement surface of the open end of the first cup and the second cup to seal the scrubbing device. In one or more embodiments, the first peelable seal and second peelable seal comprises a moisture barrier.

The first cup and the second cup are made from any type of plastic materials such as polycarbonate, polypropylene, polyethylene, polyethylene terephthalate, polylactide, acrylonitrile butadiene styrene or any other moldable plastic material used in medical devices. In one or more embodiments, the first cup and the second cup comprise a polypropylene or polyethylene material.

Another aspect of the present disclosure pertains to an assembly comprising the scrubbing device of the disinfection device of one or more embodiments connected to a syringe assembly. The syringe assembly includes a syringe barrel having an elongate body defining a chamber, an open proximal end having a flange and a distal end having a tip having a passageway therethrough in fluid communication with the chamber. The distal end of the barrel also includes a locking luer-type collar concentrically surrounding the tip. The locking luer-type collar has an internal thread. Syringe assembly further includes a stopper connected to an elongate plunger rod having a thumb press at its proximal end. In one or more embodiments, the assembly may further include a medical connector is selected from a male luer connector, a female luer connector, and needleless connector.

Another aspect of the present disclosure pertains to a method of disinfecting a medical connector, the method comprising: connecting a disinfection device of an embodiment of the present disclosure to a medical connector, wherein connecting includes removing the second cup from the syringe assembly, peeling the top web of the first peelable seal from the first cup; inserting the needle-free connector ("NFC") into the chamber of the first cup and contacting the NFC with the first absorbent material soaked with disinfectant or the antimicrobial agent; this is followed by removing the first cup of the scrubbing device from the syringe barrel by applying a torque on the entire assembly thus unthreading scrubbing device from the locking luer-type collar at the distal end of barrel; attaching the flush syringe to an IV catheter line by engages the threads of the luer lock collar on the distal end of the syringe barrel to connect the NFC to the flush syringe and flushing the IV line; unthreading the flush syringe from the NFC and peeling the top web from the second cup to expose the second absorbent material soaked in the second disinfectant, inserting the NFC into the chamber of the first cup and contacting the NFC with the first absorbent material soaked with disinfectant or the antimicrobial agent.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

FIG. 10 illustrates a perspective side view of a scrubbing element according to an exemplary second embodiment of the disclosure;

FIG. 11 illustrates a perspective view of the scrubbing element with the second cup detached from the first cup in accordance with an exemplary second embodiment of the disclosure;

FIG. 19 illustrates a perspective view of a disinfection unit 400 according to an exemplary fourth embodiment of the disclosure;

FIG. 20 illustrates a cross-sectional view of a disinfection unit 400 according to an exemplary fourth embodiment of the disclosure;

DETAILED DESCRIPTION

Figure 2:
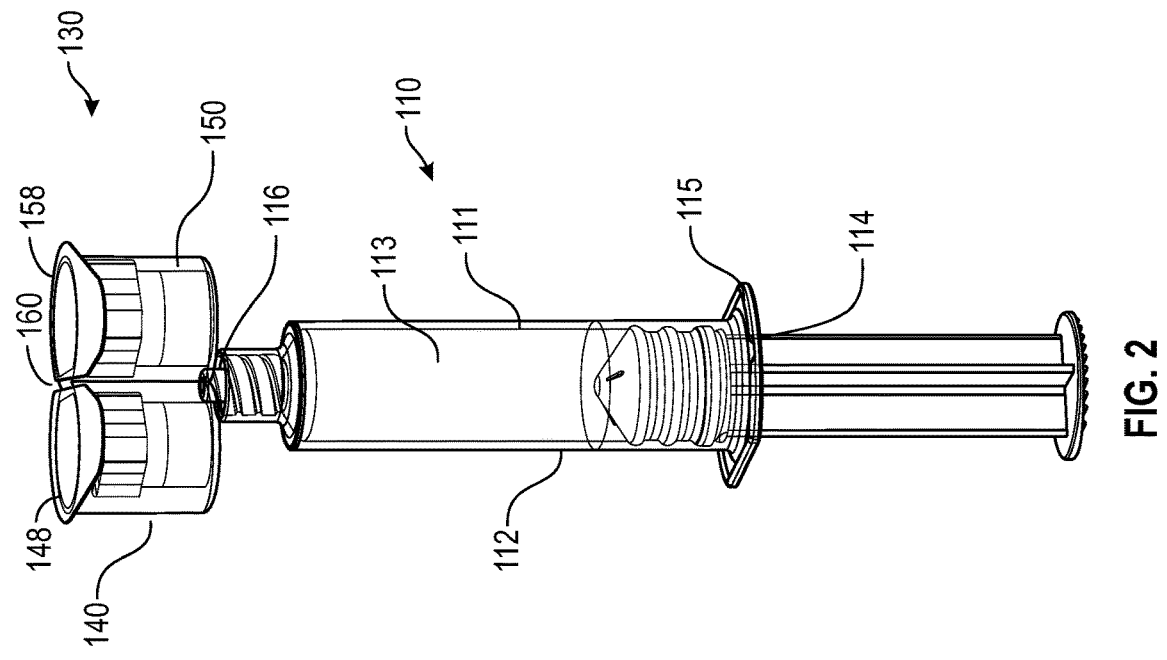
FIG. 2 illustrates a cross-sectional view of a disinfection unit 100 in accordance with an exemplary first embodiment of the disclosure.

In the current practice of SASH (Saline-Administration-Saline-Heparin) workflow, a clinician removes the disinfecting cap attached to the dwelling catheter hub to be flushed and proceeds to scrub the hub using a disinfecting wipe or scrubbing device. Next, the clinician flushes the intravenous (IV) line using a Flush syringe to make sure the catheter is working before infusing. After the first flush, the clinician then scrubs the hub using a disinfecting wipe or scrubbing device and administers a drug in the IV line. After drug administration, the clinician again scrubs the hub using a disinfecting wipe or scrubbing device. The clinician then performs a second flush of the IV line using a Flush syringe to remove any medication left in your catheter and scrubs the hub using a disinfecting wipe or scrubbing device. The clinician then "locks" the IV line using a lock syringe filled with a heparin flush to help prevent blood clots from forming in the catheter. Finally, a new disinfecting cap is attached to the dwelling catheter hub. Thus, current practice requires 4 scrubbing devices, 2 flush syringes, 1 disinfecting cap and 1 lock syringe.

Before describing several exemplary embodiments of the present disclosure, it is to be understood that the disclosure is not limited to the details of construction or process steps set forth in the following description. The disclosure is capable of other embodiments and of being practiced or being carried out in various ways.

Embodiments of the present disclosure pertain to a disinfection unit for connection to a medical connector including a syringe assembly with two integrated disinfection units assembled to the syringe assembly for connection to and disinfection of corresponding medical connectors, including threaded connectors. In one or more embodiments, the connectors are male luer connectors or female luer connectors. The disclosure aims to provide a mechanism capable of disinfecting both the lumen of open luers and the corresponding IV connector while minimizing additional steps in medical administration. It is contemplated that the disinfection unit disclosed herein can be utilized with male or female threaded connectors. The disclosure aims to provide a mechanism to disinfect an IV needleless connector during syringe use, therefore saving the clinician time and reducing work steps. The disclosure aims to reducing the number of steps required in preventing contamination of a vascular access device (VAD).

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together with a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As used herein, the term "syringe" refers to a simple pump-like device consisting of a plunger rod that fits tightly in a barrel or tube. The plunger rod can be pulled or advanced along inside the barrel, allowing the syringe to take in and expel a liquid or gas through an opening at the open end of the barrel. In one or more embodiments, the syringe is a flush syringe filled with a flush solution.

Reference to "pre-filled syringe assembly" includes syringes which have barrels filled prior to delivery to the user with a solution or medicament during or after the assembly of the syringe using sterile filling methods. Pre-filled syringe assembly include syringe assemblies are indicated for use in the flushing of vascular access devices (VADs).

As used herein, the term "medical device" refers to common medical devices having threaded or interlocking connections, the connections having corresponding mating elements. By way of example but not limitation, a syringe has a male threaded connection which releasably interlocks with a secondary medical device such as a female luer connection of a catheter, an IV line and the like. The threaded connection includes a lumen defining a fluid path surrounded by a protruding wall having the threaded means for attaching to the secondary medical device.

As used herein, the term "disinfectant" includes antimicrobial agents.

As would be readily appreciated by skilled artisans in the relevant art, while descriptive terms such as "thread", "tab", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness. Before describing several exemplary embodiments of the disclosure, it is to be understood that the disclosure is not limited to the details of construction or process steps set forth in the following description. The disclosure is capable of other embodiments and of being practiced or being carried out in various ways.

Clinicians need to handle multiple components while accessing an intravenous (IV) line or catheter as they are required to open and disinfect the hub, open the syringe, hold the line in place, etc. while ensuring that none of the devices touch any surfaces as this would lead to contamination and blood stream infections which can have deadly outcomes. Therefore, accessing an intravenous (IV) line or catheter is not straightforward and requires a certain level of dexterity to carry out the procedure while preventing the syringe tip from coming into contact with the surrounding environment. If the syringe tip touches any non-sterile surfaces, "touch" contamination can occur which can cause microbial growth in the IV line and consequently lead to incidents of catheter-associated-bloodstream infection ("CRBSI") and central line—associated bloodstream infection ("CLABSI") which are very costly and lethal.

Embodiments of the present disclosure relate to a disinfection unit including a pre-filled syringe assembly having two integrated disinfection units assembled to the syringe. The disinfection unit provides means of mechanical and chemical disinfection, i.e. a scrubbing unit (foam, etc.) and a chemical disinfectant (alcohol, etc.).

The flush syringe contains flush solution e.g. saline or other medication through the shelf life of the product and enables delivery of this saline during use, i.e. the syringe is connected to a hub (such as needle-free connectors, etc.) and the syringe contents are delivered.

The disinfection unit provides means of disinfection of the hub, through mechanical and chemical disinfection. The disinfection unit contains the chemical disinfectant (such as Isopropyl alcohol 70%) through the shelf life of the product.

As discussed below, embodiments of the present disclosure allow for non-permanently joining the disinfection unit to the syringe unit for performing the disinfection and the following flushing process in standard SASH procedures. Embodiments of the present disclosure provide non-permanent mechanical or chemical means (e.g. adhesive) of joining the disinfection units to the syringe. Embodiments of the present disclosure engage the disinfection unit and the syringe tip or thumb press on the assembly line, using adhesive, threaded connection or flexible elements, e.g. clips, on the syringe or the disinfection unit. The threaded connection or flexible elements, e.g. clips, tabs, etc., may be disposed on either the disinfection unit or the syringe (engage to a corresponding mating feature on the other component, lock, and prevent disengagement once the disinfection unit and the syringe tip cap are assembled until desired use by a clinician). In one or more embodiments, an adhesive may be applied on a contact surface between two disinfection units to bond the two disinfection units and prevent disengagement until desired use by a clinician).

Referring now to the drawings, wherein like reference numerals designate identical or corresponding parts throughout the several views, embodiments of the present disclosure are described as follows.

Referring to FIGS. 1-6, the disinfection unit 100 for connection to a medical connector according to a first exemplary embodiment of the present disclosure also generally includes a scrubbing device 130 having a first cup 140 and a second cup 150. A bottom wall 131 spans the first cup 140 and a second cup 150.

Figure 1:
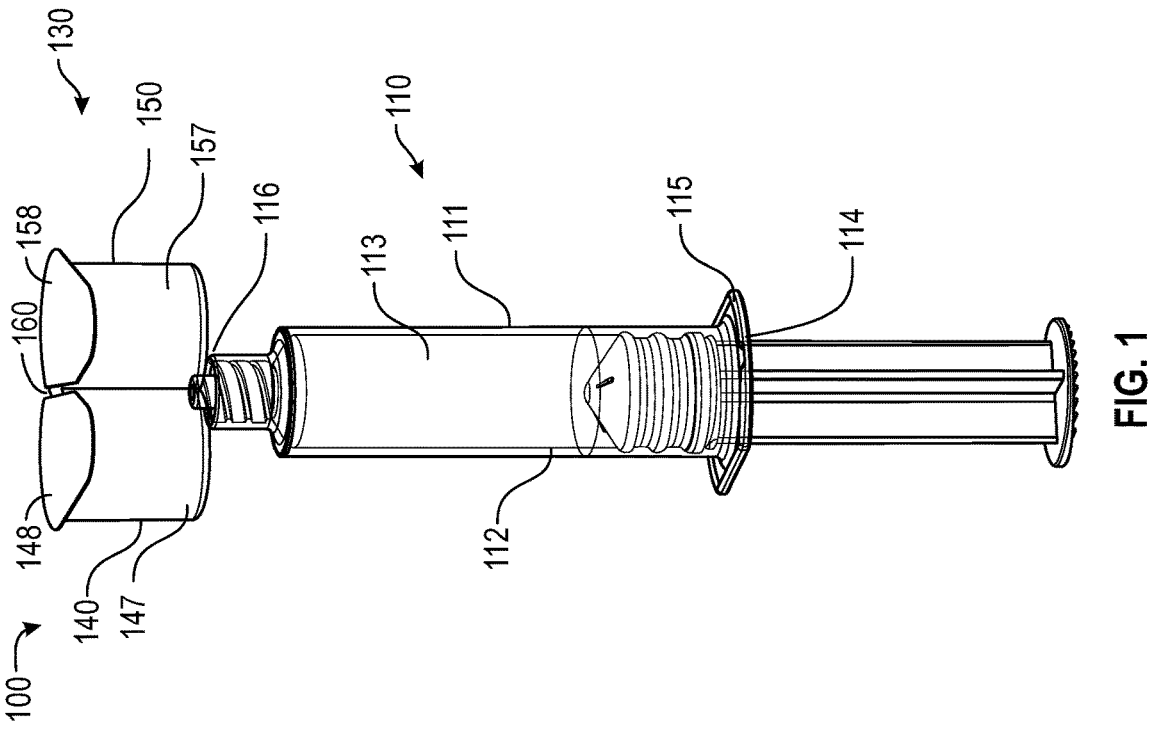
FIG. 1 illustrates a perspective view of a disinfection unit 100 according to an exemplary first embodiment of the disclosure.
Figure 4:
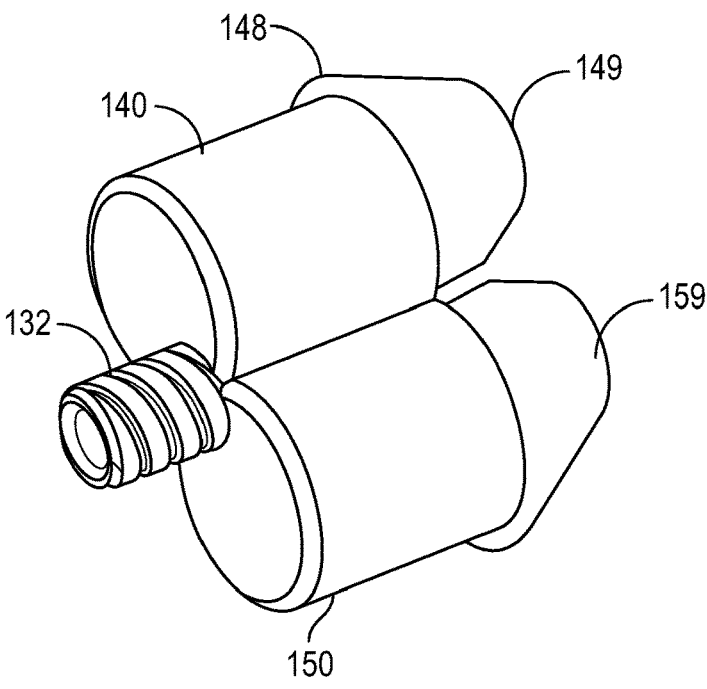
FIG. 4 illustrates a perspective bottom view of a scrubbing element according to an exemplary first embodiment of the disclosure.

Referring to FIG. 1, an assembly for connection to a medical connector includes a syringe assembly 110 having a syringe barrel 111 having an elongate body 112 defining a chamber 113 for retaining fluid. Referring to FIG. 4 the syringe barrel 111 includes an open proximal end 114 having a flange 115 and a distal end 116 including a tip 117 having a passageway 118 therethrough in fluid communication with the chamber. The distal end 116 of the barrel also includes a locking luer-type collar 119 concentrically surrounding tip 117. The locking luer-type collar 119 has an internal thread 120. Syringe assembly 110 further includes a stopper 121 connected to an elongate plunger rod 122 having a thumb press 123 at its proximal end.

Figure 5:
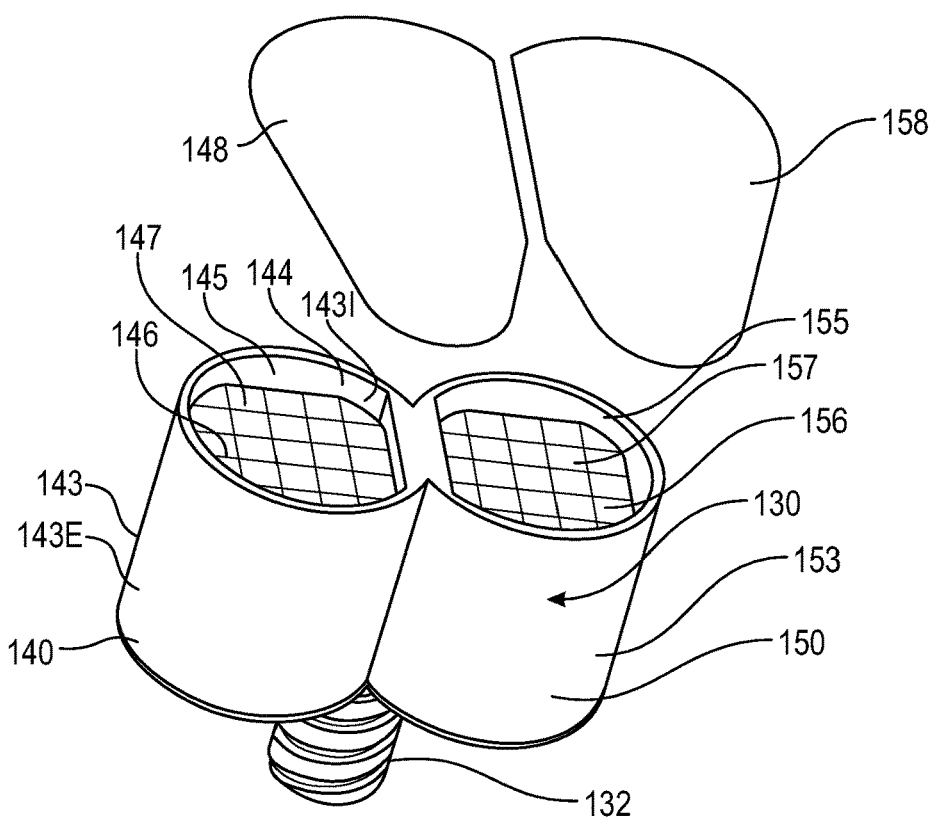
FIG. 5 illustrates a perspective top view of a scrubbing element in accordance with an exemplary first embodiment of the disclosure.

Referring to FIGS. 1-5, the first cup 140 comprises an integral body 141, a closed end 142, an annular wall 143 having a length $L_C$ extending from the closed end 142 to an open end 144 that defines a chamber 145 containing a first absorbent material 146, a first disinfectant in the first cup 140, and a first peelable seal 148. The first absorbent material 146 is soaked in the first disinfectant. The open end 144 defines an engagement surface to contact the first peelable seal 148 having a top web 149. Referring to FIGS. 1 and 5, the annular wall 143 of the first cup 140 comprises an exterior wall surface 143E and an interior wall surface 1431. The interior wall surface 1431 defines an opening adjacent the open end 144.

Referring to FIGS. 1-6, the second cup 150 comprises an integral body 151, a closed end 152, an annular wall 153 having a length $L_C$ extending from the closed end 152 to an open end 154 that defines a second chamber 155 containing a second absorbent material 156, a second disinfectant 157 in the second cup 150, and a second peelable seal 158 having a top web 159. The second absorbent material 156 is soaked in the second disinfectant 157 or the antimicrobial agent. The open end 154 defines an engagement surface to contact the second peelable seal 158. Referring to FIGS. 1 and 5, the annular wall 153 of the second cup 150 comprises an exterior wall surface 153E and an interior wall surface 153I. The interior wall surface 153I defines an opening adjacent the open end 154.

The first cup 140 and the second cup 150 are disposed in a side-by-side orientation and the first cup 140 and the second cup 150 are bounded or circumscribed by a common dividing wall 160.

Figure 3:
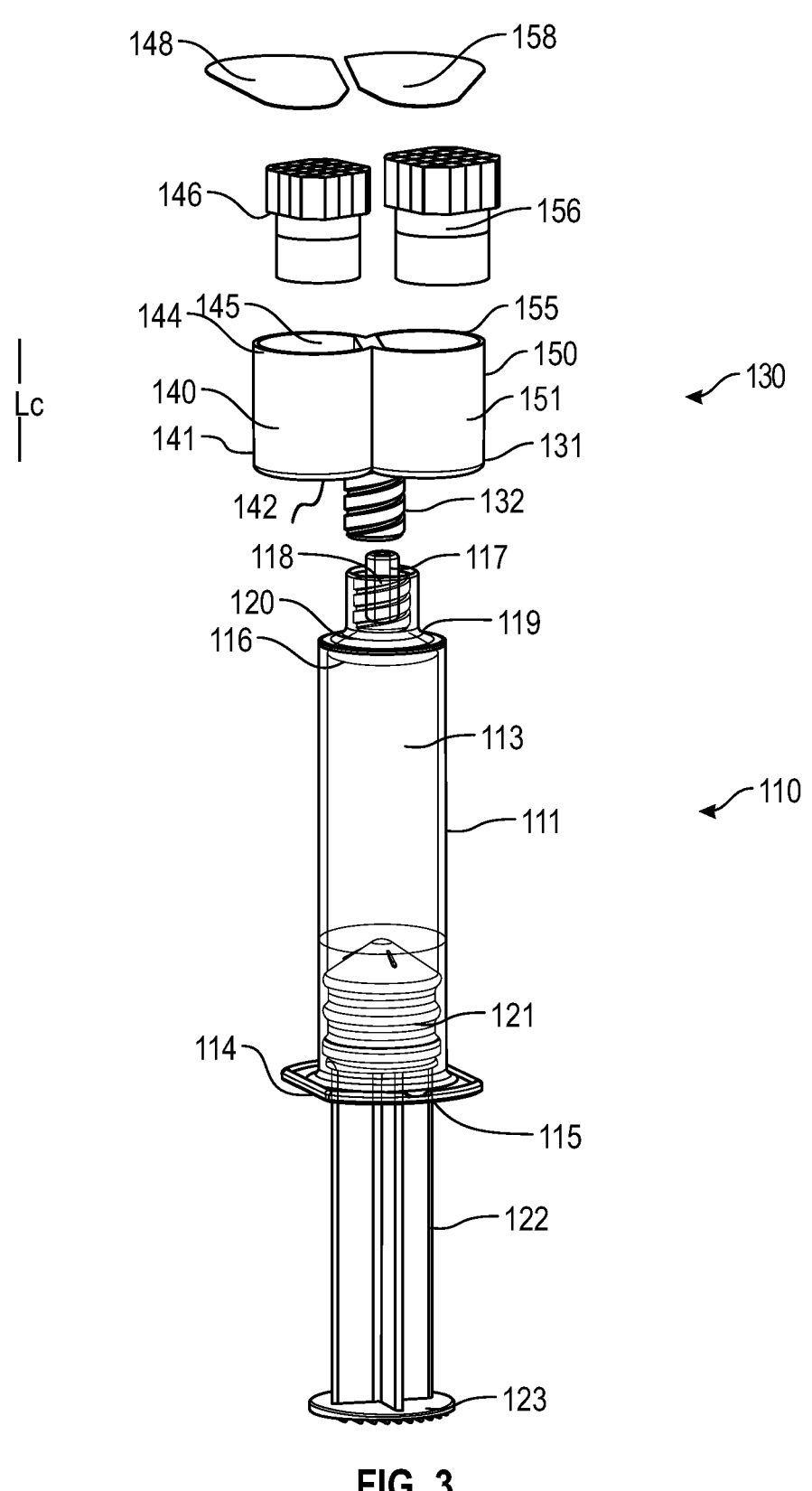
FIG. 3 illustrates an exploded perspective view of a disinfection unit 100 in accordance with an exemplary first embodiment of the disclosure.

As shown in FIGS. 1-3, syringe assembly 110 can be attached to scrubbing device 130 having mechanical mating features. Once assembled, the assembly of the syringe assembly 110 and scrubbing device 130 can withstand, axial, radial, disassembly forces. To remove the scrubbing device 130 from the syringe barrel, the user shall apply a torque on the entire assembly thus unthreading scrubbing device 130 from the locking luer-type collar 119 at the distal end of barrel to allow attachment of the flush syringe to the IV catheter line. When a torque is applied to either the syringe or scrubbing device 130 or both, the scrubbing device 130 should unthread off the barrel.

In the prior art, a "cradle" underside is employed under where the disinfecting unit is held resulting in the cradle being easily disassembled by a user during normal use. The assembly of the scrubbing device 130 and collar of the syringe of the present disclosure does not require a separate "cradle" or other device to assemble the devices together.

In one or more embodiments shown in FIGS. 1-3, the mechanical mating and assembly features ensure that the device can be assembled in an automated process and ensure device integrity during transport, use, and over the course of the product's shelf life. The assembly of the scrubbing device 130 and collar of the syringe of the present disclosure via a mechanical connection or threaded connection facilitates high speed, automated assembly.

Compared to separate flush syringe and disinfection unit products that are currently available, embodiments of the integrated disinfection unit of the present disclosure provides easy access to the disinfection product at each flush and easier hand operation during disinfection followed by flushing.

In one or more embodiments, the disinfection unit 100 includes a connection element allowing it to be connected to a syringe. In one or more embodiments, the connection element is a threaded connection, for example, luer threaded connection to allow the assembled disinfection unit 100 to be connected to a syringe. In an exemplary implementation of the embodiments of present disclosure, the disinfection unit 100 includes integrated threads or tabs, and other features in any and all combinations allowing it to interface with a threaded fitting of a medical device. In one or more embodiments, the syringe assembly 110 can be attached to scrubbing device 130 using various methods including, but not limited to, mechanical fasteners, snap-fittings, and threaded connection. In one or more embodiments, a threaded connection is disposed on the bottom exterior surface of the disinfection unit 100 having threads that are sized and pitched to engage threads of a luer lock collar on the distal end of the syringe barrel to allow the assembled disinfection unit 100 to be connected to a syringe. In one or more embodiments as shown in FIG. 1, the bottom wall 131 of the scrubbing device 130 includes a threaded post 132 disposed in the center of the bottom wall 131 adjoining the common dividing wall 160 that corresponds to the internal thread 120 of the locking luer-type collar 119 on the distal end of the syringe barrel 111. In one or more alternate embodiments, a dividing wall 160 may separate a single cup into two separate cups.

Figure 6:
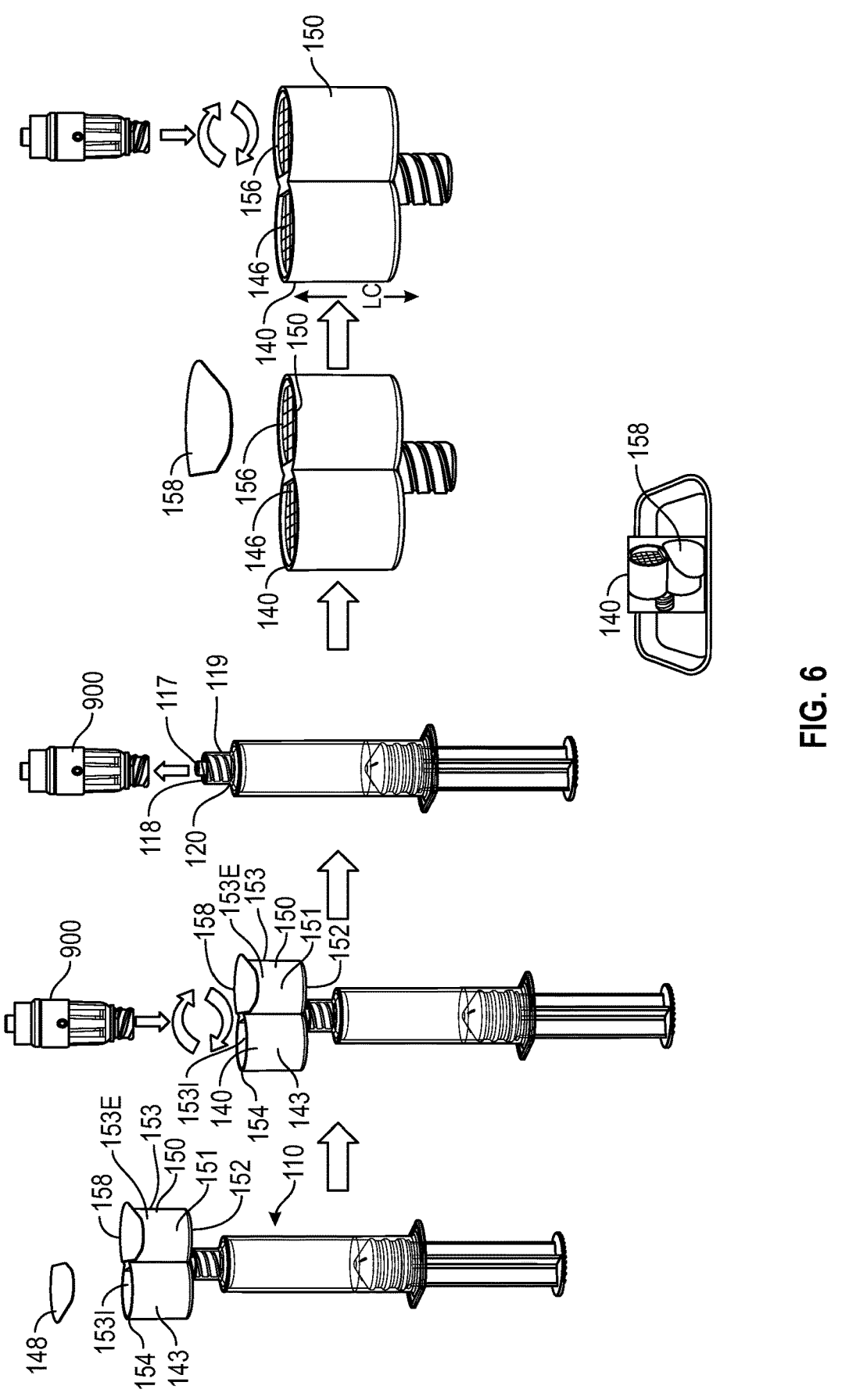
FIG. 6 illustrates a flow chart of a disinfection process using a disinfection unit 100 in accordance with an exemplary first embodiment of the disclosure.
Figure 8:
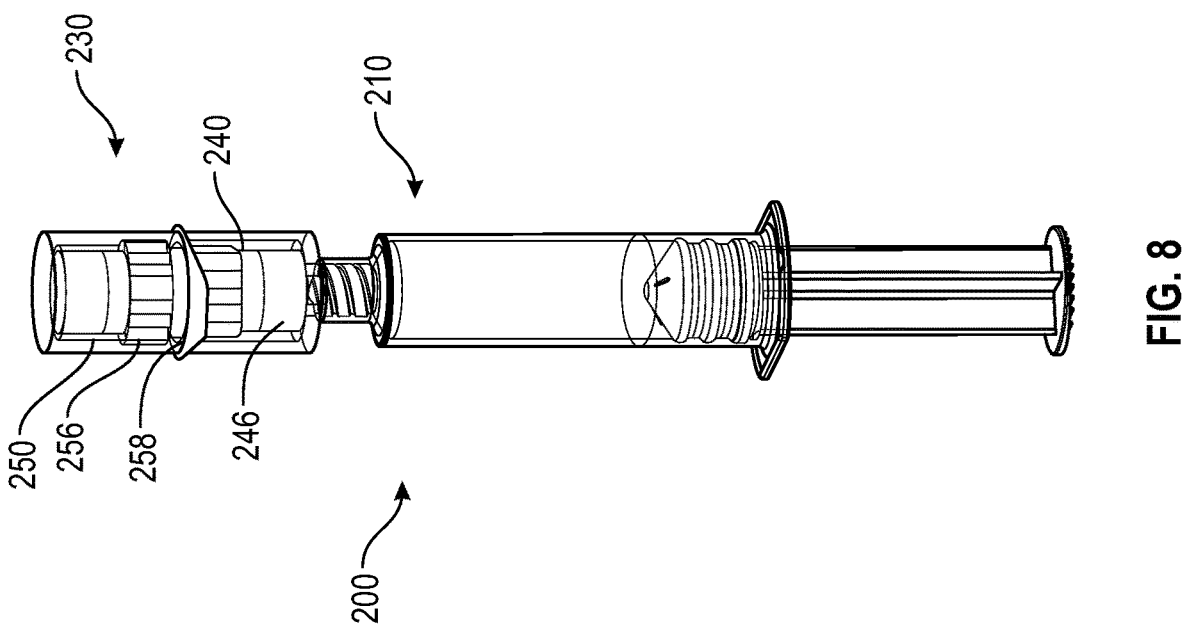
FIG. 8 illustrates a cross-sectional view of a disinfection unit 200 according to an exemplary second embodiment of the disclosure.

Referring FIG. 6 the scrubbing device 130 can achieve disinfection when used on needle-free connector ("NFC") medical connectors 900 by integrating a first disinfectant 147 in the first absorbent material 146 disposed and housed in the first chamber 145 of the first cup 140 and a second disinfectant 157 in the second absorbent material 156 disposed and housed in the second chamber 155 of the second cup 150. The first disinfectant (147) and second disinfectant (157) can be directly included in the first chamber 145 and second chamber 155 respectively and can be absorbed into first absorbent material 146 and into second absorbent material 156 (e.g. sponges or foam material) that fills the chamber of first cup 140 and second cup 150 respectively. The scrubbing device 130 is designed to be compatible in interacting with various disinfectants. In one or more embodiments, the first disinfectant 147 or second disinfectant 157 may include variations of alcohol or chlorhexidine. In one or more embodiments, the first disinfectant 147 or second disinfectant 157 is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the first disinfectant 147 or second disinfectant 157 comprises at least one of chlorhexidine gluconate and chlorhexidine diacetate. In one or more embodiments, the first disinfectant 147 or second disinfectant 157 is a fluid or a gel.

First absorbent material 146 soaks up the first disinfectant 147 or the antimicrobial agent that is housed within the chamber 145 of the first cup 140. In one or more embodiments, the first absorbent material 146 is a nonwoven material, foam, or a sponge. In a specific embodiment, the foam is a polyurethane foam. In a specific embodiment the second absorbent material 156 is in the form of a foam plug. In one or more embodiments, the second absorbent material 156 includes one or more slits as shown in FIGS. 3 and 5.

A first peelable seal 148 having a top web 149 is disposed on the engagement surface of first cup 140 to prevent the first absorbent material 146 from exiting the chamber 145. With the first absorbent material 146 properly inserted into the chamber 145 of the first cup 140, the first peelable seal 148 may be secured to the engagement surface of the open end 144 of first cup 140 to seal the scrubbing device 130.

Second absorbent material 156 is disposed and housed in the second chamber 155 of the second cup 150 and soaks up the second disinfectant 157 or the antimicrobial agent that is housed within the second chamber 155 of the second cup 150. In one or more embodiments, the second absorbent material 156 is a nonwoven material, foam, or a sponge. In a specific embodiment, the foam is a polyurethane foam. In a specific embodiment the second absorbent material 156 is in the form of a foam plug. In one or more embodiments, the second absorbent material 156 includes one or more slits as shown in FIGS. 2-6.

A second peelable seal 158 having a top web 159 is disposed on the engagement surface of second cup 150 to prevent the second absorbent material 156 from exiting the second chamber 155. With the second absorbent material 156 properly inserted into the second chamber 155 of the second cup 150, the second peelable seal 158 may be secured to the engagement surface of the open end 154 of second cup 150 to seal the scrubbing device 130.

The first peelable seal 148 and second peelable seal 158 minimize entry of potential particulate hazard and provides a substantially impermeable enclosure for the scrubbing device 130, provides a leak prevention and protection enclosure, protects the contents of first absorbent material 146 and second absorbent material 156 contained within the first chamber 145 and second chamber 155, respectively and/or maintains a sealed, sterilized environment. The first peelable seal 148 and second peelable seal 158 provides a sufficient seal at a range of temperatures, pressures, and humidity levels. Referring to FIG. 1, first peelable seal 148 and second peelable seal 158 may be disposed on the respective open ends (144, 154) of the first cup 140 and second cup 150 to prevent the pre-filled first and second disinfectant (147, 157) from exiting the chamber of the respective first cup 140 and second cup 150.

The first peelable seal 148 and second peelable seal 158 can be a plastic sealed aluminum, and can be chemically-resistant, light-blocking, non-permeable, or sterile In one or more embodiments, the first peelable seal 148 and second peelable seal 158 comprises an aluminum or multi-layer polymer film peel back top. In a specific embodiment, the first peelable seal 148 and second peelable seal 158 is heat-sealed or induction sealed to the engagement surface of the open end (144, 154) of first and second cups (140,150) to seal the scrubbing device 130. In one or more embodiments, the first peelable seal 148 and second peelable seal 158 comprises a moisture barrier.

The first absorbent material 146 and second absorbent material 156 and the disinfectant or the antimicrobial agent contacts the male luer connector, the female luer connector, and the hemodialysis connector after insertion of the connector into the open end (144, 154) of the respective cups 140 and 150.

In one or more embodiments, the female connector may be selected from the group consisting essentially of needle-free connectors, catheter luer connectors, stopcocks, and hemodialysis connectors. In one or more embodiments, the male connector may be an intravenous tubing end, a stop-cock or male lock luer.

The first cup 140 and the second cup 150 are made from any type of plastic materials such as polycarbonate, polypropylene, polyethylene, polyethylene terephthalate, polylactide, acrylonitrile butadiene styrene or any other moldable plastic material used in medical devices. In one or more embodiments, the first cup 140 and the second cup 150 comprises a polypropylene or polyethylene material.

To avoid having to use different types of disinfecting caps to clean different types of connectors, disinfection device 100 with first cup 140 and second cup 150 is compatible and engages with male luer connectors and also with female luer connectors thereby allowing the user to clean different types of connectors with a single device. Upon mounting the first cup 140 and second cup 150 onto female luer connectors, or a male luer connector, the female or male medical connector engage the interior wall upon insertion into the first chamber

145 or second chamber 155 and contact the first absorbent material 146 and into second absorbent material 156 soaked with disinfectant or the antimicrobial agent. Hence, the device of the present disclosure can disinfect both male and female luer connectors, thus fulfilling a current need in the art.

Other aspects of the present disclosure are directed to methods of disinfecting medical connectors and assemblies. In one or more embodiments, a method of disinfecting a medical connector comprises connecting the device of one or more embodiments to a medical connector, wherein connecting includes frictionally engaging the interior wall surface upon insertion into the chamber such that the medical connector contacts the absorbent material and the disinfectant or antimicrobial agent.

In use, a clinician peels the top web 149 of the first peelable seal 148 from the first cup 140 before flushing an IV line. The clinician then disinfects the NFC using the first cup 140. Upon insertion of the NFC into the first cup 140, the first absorbent material 146 soaked with first disinfectant 147 contacts the NFC. In one or more embodiments the NFC may be a male luer connector, the female luer connector, or the hemodialysis connector. Next, the clinician removes scrubbing device 130 from the syringe barrel, by applying a torque on the entire assembly thus unthreading scrubbing device 130 from the locking luer-type collar 119 at the distal end of barrel 111 to allow attachment of the flush syringe to the IV catheter line to flush the IV line. The clinician places the first cup 140 on a sterile tray for subsequent use of the second cup and engages threads of the luer lock collar on the distal end of the syringe barrel to the NFC to connect the NFC to the flush syringe. The clinician then proceeds with flushing the IV line. Next, the clinician picks up detached scrubbing device 130 and peels top web 159 from second cup 150 after flushing IV line to expose the second absorbent material 156 soaked in the second disinfectant 157 and disinfects the NFC using the second cup 150 in which the second absorbent material 156 soaked in the second disinfectant 157 or the antimicrobial agent in the second cup 150 contacts the male luer connector, the female luer connector, and the hemodialysis connector after insertion of the NFC connector into second cup 150. As in current practice, the clinician then administers medicine and performs a second flush of the IV line using a Flush syringe to remove any medication left in your catheter and scrubs the hub using a disinfecting wipe or scrubbing device. The clinician then "locks" the IV line using a lock syringe filled with a heparin flush to help prevent blood clots from forming in the catheter. Finally, a new disinfecting cap is attached to the dwelling catheter hub.

In the current practice wherein the clinician has only one scrubbing device attached to a flush syringe the integrated scrubbing device is used before flushing. However, after the primary flushing there is no second scrubbing device attached to the syringe to disinfect the catheter hub. Embodiments of the present disclosure provide additional scrubbing device integrated with the flush syringe, eg. a flush syringe with two disinfecting/scrubbing devices, which allow the clinician to disinfect the hub before and after flushing thus leading to compliance with SASH because the clinician does not need to look for a disinfecting device or skip the connector disinfection before initiating the next process (e.g. administration of medicine).

As noted above, currently available products and SASH practice does not address any cleaning after the initial flushing process as the sanitization ends after the first flush. The benefit of the embodiments of the present invention which includes the two individually packaged first cup 140 and second cup 150 both having disinfectant-loaded absorbent materials (146,156) is institution of a two-step sanitization that provides additional protection to the patient by including an additional cleaning step using the IPA or scrubbing device to sanitize the hub or connecting interface prior to medication or lock solution administration thereby further preventing potential infections to the patient.

When using the first cup 140, compression of the first absorbent material 146 toward the closed end 142 of the chamber 145 upon connection to the female luer connector or the male luer connector allows the connector to contact the first disinfectant 147 to disinfect the female luer connector or the male luer connector. Similarly, when using the second cup 150, compression of the second absorbent material 156 toward the closed end 152 of the second chamber 155 upon connection to the female luer connector or the male luer connector allows the connector to contact the second disinfectant 157 to disinfect the female luer connector or the male luer connector.

In one or more embodiments, an assembly comprises the device of one or more embodiments connected to a medical connector. In one or more embodiments, the medical connector is selected from a male luer connector, a female luer connector, and needleless connector.

Referring to FIGS. 7-12, the disinfection assembly 200 for connection to a medical connector according to an exemplary embodiment of the present disclosure also generally includes a syringe assembly 210 having a syringe barrel 211 having an elongate body 212 defining a chamber 213 for retaining fluid. The syringe barrel 211 includes an open proximal end 214 having a flange 215 and a distal end 216 including a tip 217 having a passageway 218 therethrough in fluid communication with the chamber. The distal end 216 of the barrel also includes a locking luer-type collar 219 concentrically surrounding tip 217. The locking luer-type collar 219 has an internal thread 220. Syringe assembly 210 further includes a stopper 221 connected to an elongate plunger rod 222 having a thumb press 223 at its proximal end, a scrubbing device 230 having a first cup 240 and a second cup 250. A bottom wall 231 spans the first cup 240.

Figure 7:
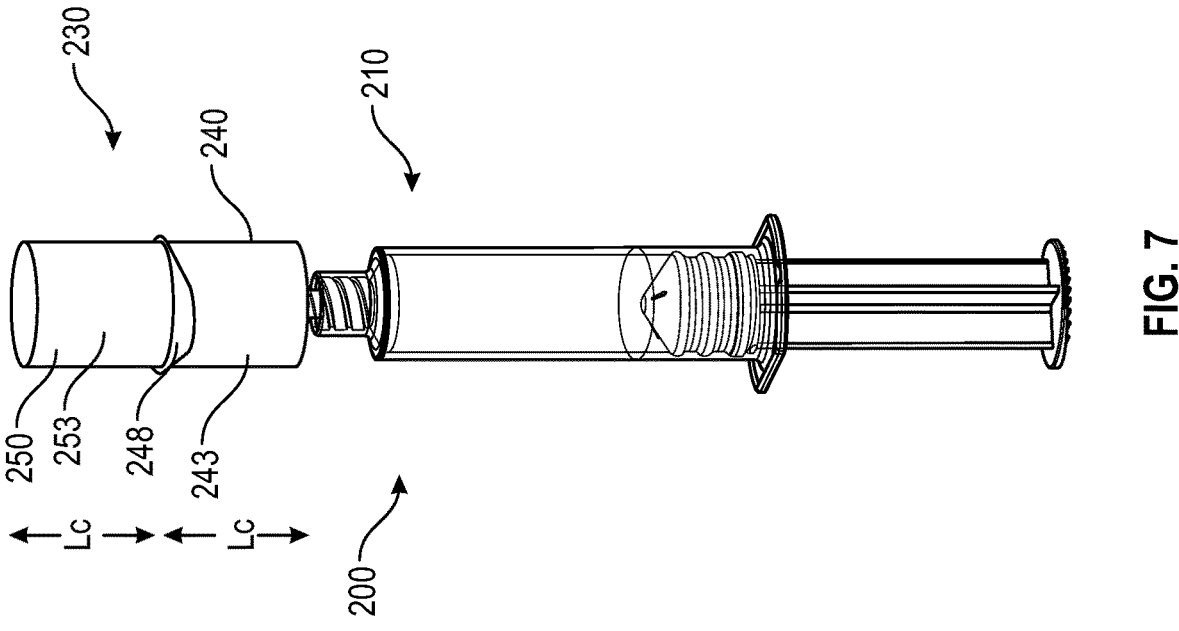
FIG. 7 illustrates a perspective view of a disinfection unit 200 according to an exemplary second embodiment of the disclosure.

Referring to FIG. 7, the first cup 240 comprises an integral body 241, a closed end 242, an annular wall 243 having a length $L_C$ extending from the closed end 242 to an open end 244 that defines a chamber 245 containing a first absorbent material 246, a first disinfectant 247 in the first cup 240, and a peelable seal 248 having a top web 249. The peelable seal 248 has a bottom surface 248B and a top surface 248T. The first absorbent material 246 is soaked in the first disinfectant 247 or the antimicrobial agent. The open end 244 defines an engagement surface to contact bottom surface 248B of the peelable seal 248.

Figure 9:
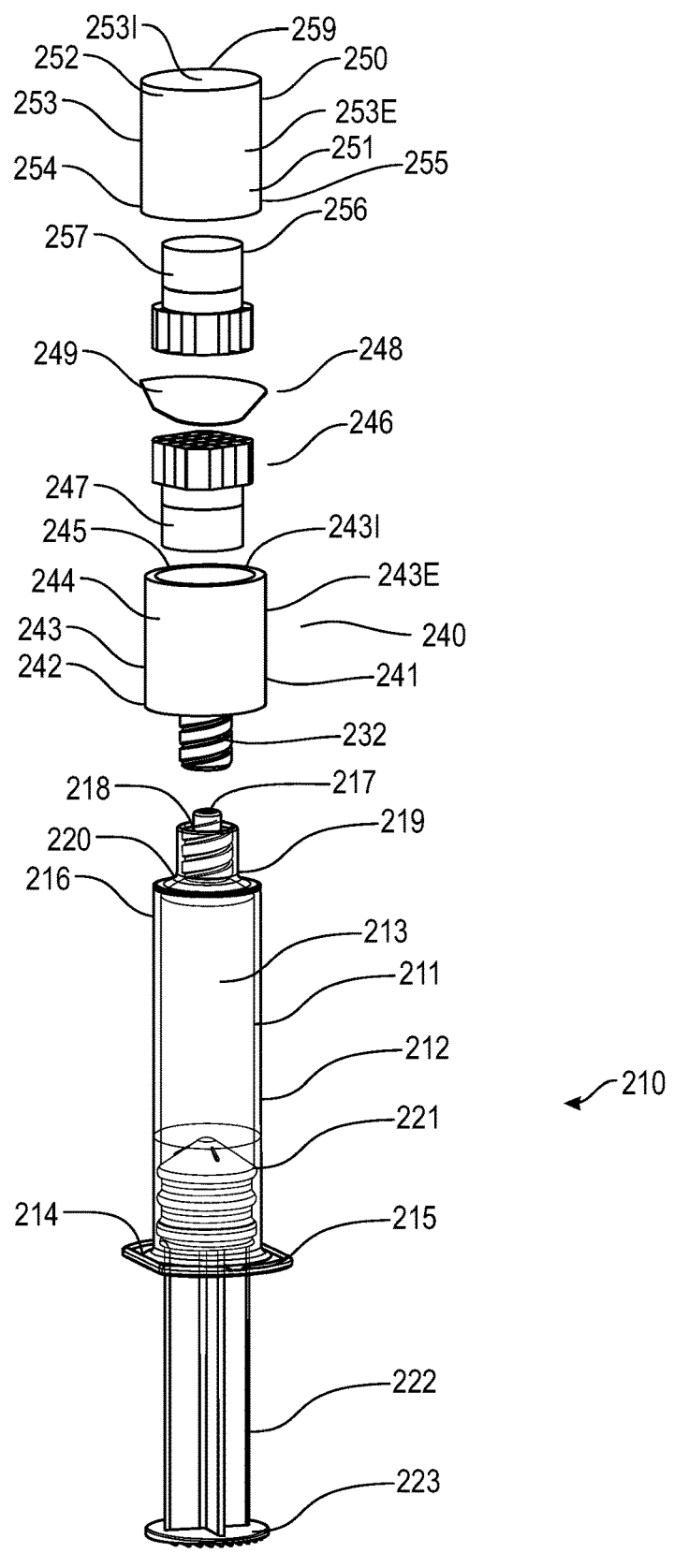
FIG. 9 illustrates an exploded perspective view of a disinfection unit 200 according to an exemplary second embodiment of the disclosure.

Referring to FIG. 9, the second cup 250 comprises an integral body 251, a closed end 252, an annular wall 253 having a length $L_C$ extending from the closed end 252 to an open end 254 that defines a second chamber 255 containing a second absorbent material 256, a second disinfectant 257 in the second cup 250. The second absorbent material 256 is soaked in the second disinfectant 257 or the antimicrobial agent. The open end 254 defines an engagement surface to contact the top surface 248T of the peelable seal 248. Referring to FIG. 9, the annular wall 253 of the second cup 250 comprises an exterior wall surface 253E and an interior wall surface 2531. The interior wall surface 2531 defines an opening adjacent the open end 254.

The first cup 240 and the second cup 250 are disposed in a top-bottom orientation and the first cup 240 and the second cup 250 are bounded or circumscribed by a common peelable seal 248 in which the open end 244 of the first cup 240 defines an engagement surface to contact bottom surface 248B of the peelable seal 248 and the open end 254 of the second cup 250 defines an engagement surface to contact the top surface 248T of the peelable seal 248.

As shown in FIGS. 7-12, syringe assembly 210 can be attached to the first cup 240 of scrubbing device 230 by a mechanical mating features. Once assembled together, the assembly of the syringe assembly 210 and first cup 240 of scrubbing device 230 can withstand, axial, radial, disassembly forces. To remove the first cup 240 of scrubbing device 230 from the syringe barrel, the user shall apply a torque on the entire assembly thus unthreading scrubbing device 230 from the locking luer-type collar 219 at the distal end of barrel to allow attachment of the flush syringe to the IV catheter line. When a torque is applied to either the syringe or first cup 240 of scrubbing device 230 or both, the scrubbing device 230 should unthread off the barrel.

In one or more embodiments shown in FIGS. 7-12, the mechanical mating and assembly features ensure that the device can be assembled in an automated process and ensure device integrity during transport, use, and over the course of the product's shelf life. The assembly of the scrubbing device 230 and collar of the syringe of the present disclosure via a mechanical connection or threaded connection facilitates high speed, automated assembly.

Compared to separate flush syringe and disinfection unit products that are currently available, embodiments of the integrated disinfection unit 200 of the present disclosure provides easy access to the disinfection product at each flush and easier hand operation during disinfection followed by flushing.

In one or more embodiments, the disinfection unit 200 includes a connection element allowing it to be connected to a syringe. In one or more embodiments, the connection element is a threaded connection, for example, luer threaded connection to allow the assembled disinfection unit 200 to be connected to a syringe. In an exemplary implementation of the embodiments of present disclosure, the disinfection unit 200 includes integrated threads or tabs, and other features in any and all combinations allowing the first cup 240 to interface with a threaded fitting of a medical device. In one or more embodiments, the syringe assembly 210 can be attached to the first cup 240 of the scrubbing device 230 using various methods including, but not limited to, mechanical fasteners, snap-fittings, and threaded connection. In one or more embodiments, a threaded connection is disposed on the bottom exterior surface of the disinfection unit 200 having threads that are sized and pitched to engage threads of a luer lock collar on the distal end of the syringe barrel to allow the assembled disinfection unit 200 to be connected to a syringe. In one or more embodiments as shown in FIG. 9-11, the bottom wall 231 of the first cup 240 of the scrubbing device 230 includes a threaded post 232 disposed in the center of the bottom wall 231 of the first cup 240 that corresponds to the internal thread 220 of the locking luer-type collar 219 on the distal end of the syringe barrel 211.

The scrubbing device 230 can achieve disinfection when used on needle-free connector ("NFC") by integrating a first disinfectant 247 in the first absorbent material 246 disposed and housed in the first chamber 245 of the first cup 240 and a second disinfectant 257 in the second absorbent material 256 disposed and housed in the second chamber 255 of the second cup 50. The first and second disinfectant (247, 257) can be directly included in the first chamber 245 and second chamber 255 and can be absorbed into first absorbent material 246 and into second absorbent material 256 (e.g. sponges or foam material) that fills the chamber of first cup 240 and second cup 250 respectively. The scrubbing device 230 is designed to be compatible in interacting with various disinfectants. In one or more embodiments, the first disinfectant 247 or second disinfectant 257 may include variations of alcohol or chlorhexidine. In one or more embodiments, the first disinfectant 247 or second disinfectant 257 is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the first disinfectant 247 or second disinfectant 257 comprises at least one of chlorhexidine gluconate and chlorhexidine diacetate. In one or more embodiments, the first disinfectant 247 or second disinfectant 257 is a fluid or a gel.

First absorbent material 246 soaks up the first disinfectant 247 or the antimicrobial agent that is housed within the chamber 245 of the first cup 240. In one or more embodiments, the first absorbent material 246 is a nonwoven material, foam, or a sponge. In a specific embodiment, the foam is a polyurethane foam. In a specific embodiment the second absorbent material 256 is in the form of a foam plug. In one or more embodiments, the second absorbent material 256 includes one or more slits as shown in FIGS. 9 and 11.

The peelable seal 248 having a top web 249 is disposed on the engagement surface of cup 240 to prevent the first absorbent material 246 from exiting the chamber 245. With the first absorbent material 246 properly inserted into the chamber 245 of the first cup 240, the peelable seal 248 may be secured to the engagement surface of the open end 244 of first cup 240 to seal the scrubbing device 230.

Figure 12:
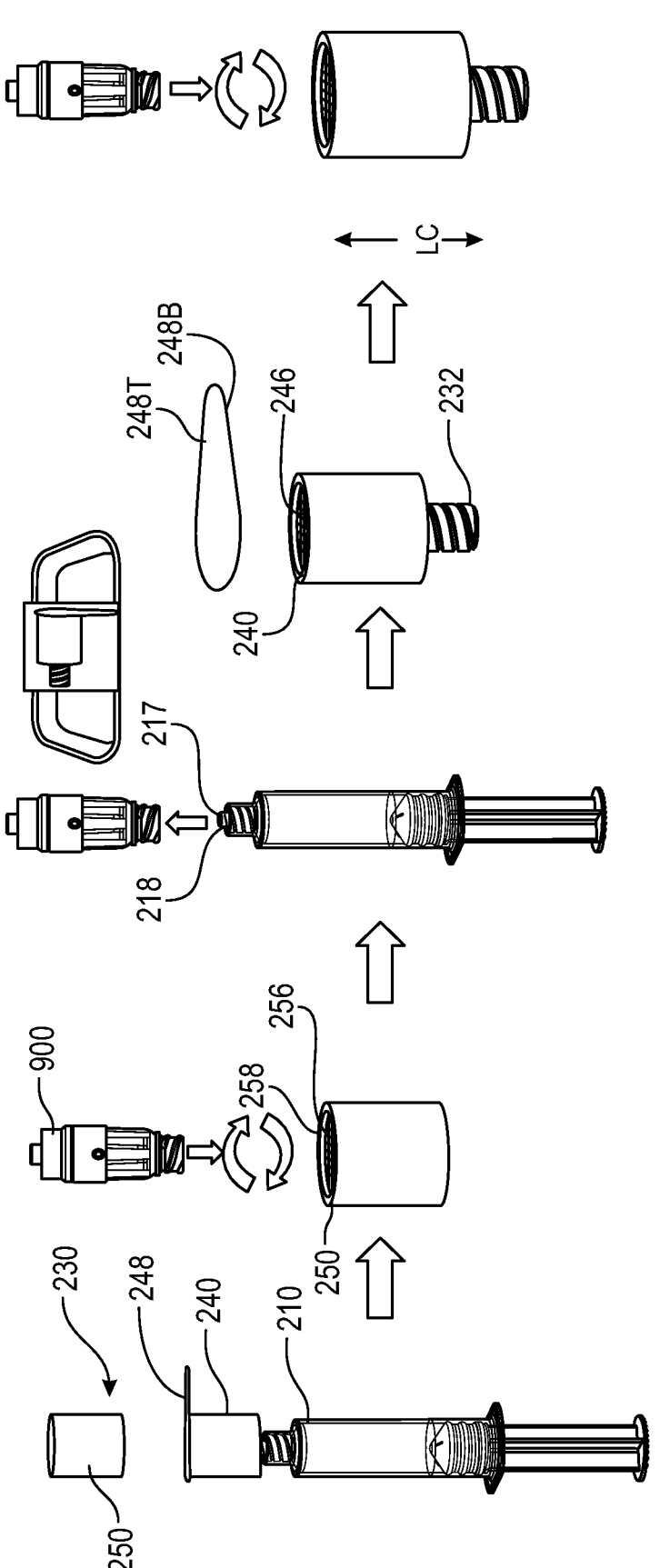
FIG. 12 illustrates a flow chart of a disinfection process using a disinfection unit 200 in accordance with an exemplary second embodiment of the disclosure.

Second absorbent material 256 is disposed and housed in the second chamber 255 of the second cup 250 and soaks up the second disinfectant 257 or the antimicrobial agent that is housed within the second chamber 255 of the second cup 250. In one or more embodiments, the second absorbent material 256 is a nonwoven material, foam, or a sponge. In a specific embodiment, the foam is a polyurethane foam. In a specific embodiment the second absorbent material 256 is in the form of a foam plug. In one or more embodiments, the second absorbent material 256 includes one or more slits as shown in FIGS. 11 and 12.

The peelable seal 248 minimizes entry of potential particulate hazard and also provides a substantially impermeable enclosure for the scrubbing device 230, provides a leak prevention and protection enclosure, protects the contents of first absorbent material 246 and second absorbent material 256 contained within the first chamber 245 and second chamber 255, respectively and/or maintains a sealed, sterilized environment. The peelable seal 248 provides a sufficient seal at a range of temperatures, pressures, and humidity levels. Referring to FIG. 9, peelable seal 248 is be disposed on the open ends (244, 254) of the first cup 240 and second cup 250 to prevent the pre-filled first and second disinfectant (247, 257) from exiting the chamber of the respective first cup 240 and second cup 250.

The peelable seal 248 can be a plastic sealed aluminum, and can be chemically-resistant, light-blocking, non-permeable, or sterile In one or more embodiments, the peelable seal 248 comprises an aluminum or multi-layer polymer film peel back top. In a specific embodiment, the peelable seal 248 is heat-sealed or induction sealed to the engagement surface of the open end (244, 254) of cup (240,250) to seal the scrubbing device 230. In one or more embodiments, the peelable seal 248 comprises a moisture barrier.

The first absorbent material 246 and second absorbent material 256 and the disinfectant or the antimicrobial agent contacts the male luer connector, the female luer connector, and the hemodialysis connector after insertion of the connector into the open end (244, 254) of the respective cups 240 and 250.

In one or more embodiments, the female connector may be selected from the group consisting essentially of needle-free connectors, catheter luer connectors, stopcocks, and hemodialysis connectors. In one or more embodiments, the male connector may be an intravenous tubing end, a stopcock or male lock luer.

The first cup 240 and the second cup 250 are made from any type of plastic materials such as polycarbonate, polypropylene, polyethylene, polyethylene terephthalate, polylactide, acrylonitrile butadiene styrene or any other moldable plastic material used in medical devices. In one or more embodiments, the first cup 240 and the second cup 250 comprises a polypropylene or polyethylene material.

To avoid having to use different types of disinfecting caps to clean different types of connectors, disinfection device 200 with first cup 240 and second cup 250 is compatible and engages with male luer connectors and with female luer connectors thereby allowing the user to clean different types of connectors with a single device. Upon mounting the first cup 240 and second cup 250 onto female luer connectors, or a male luer connector, the female or male medical connector engage the interior wall upon insertion into the chamber 245 or 255 and contact the first absorbent material 246 and into second absorbent material 256 soaked with disinfectant or the antimicrobial agent. Hence, the device of the present disclosure can disinfect both male and female luer connectors, thus fulfilling a current need in the art.

Other aspects of the present disclosure are directed to methods of disinfecting medical connectors and assemblies. In one or more embodiments, a method of disinfecting a medical connector comprises connecting the device of one or more embodiments to a medical connector, wherein connecting includes frictionally engaging the interior wall surface upon insertion into the chamber such that the medical connector contacts the absorbent material and the disinfectant or antimicrobial agent.

In use, a clinician peels the second cup 250 off the top web 249 of the peelable seal 248 to remove the second cup from the scrubbing device 230 in a manner that the peelable seal 248 remains on the first cup 240. The bond strength of the peelable seal 248 to the first cup 240 is greater than the bond strength of the peelable seal 248 to the second cup 250 thus allowing the second cup to be removed from the scrubbing device 230 while allowing the peelable seal 248 to remain on the first cup 240. The clinician then disinfects the NFC using the second cup 250. Upon insertion of the NFC 900 into the second cup 250, the second absorbent material 256 soaked with second disinfectant 257 contacts the NFC. In one or more embodiments the NFC 900 may be a male luer connector, the female luer connector, or the hemodialysis connector. Next, the clinician removes first cup 240 of the scrubbing device 230 from the syringe barrel, by applying a torque on the entire assembly thus unthreading scrubbing device 230 from the locking luer-type collar 219 at the distal end of barrel 211 to allow attachment of the flush syringe to the IV catheter line to flush the IV line. The clinician places the first cup 240 on a sterile tray for subsequent use of the first cup and engages threads of the luer lock collar on the distal end of the syringe barrel to the NFC to connect the NFC to the flush syringe. The clinician then proceeds with flushing the IV line. Next, the clinician picks up detached first cup 240 of scrubbing device 230 and peels top web 259 from first cup 240 after flushing IV line to expose the first absorbent material 246 soaked in the first disinfectant 47 and disinfects the NFC using the first cup 240 in which the first absorbent material 246 soaked in the first disinfectant 247 or the antimicrobial agent in the first cup 240 contacts the male luer connector, the female luer connector, and the hemodialysis connector after insertion of the NFC connector into first cup 240. As in current practice, the clinician then administers medicine and performs a second flush of the IV line using a Flush syringe to remove any medication left in your catheter and scrubs the hub using a disinfecting wipe or scrubbing device. The clinician then "locks" the IV line using a lock syringe filled with a heparin flush to help prevent blood clots from forming in the catheter. Finally, a new disinfecting cap is attached to the dwelling catheter hub.

As noted above, currently products and SASH practice does not address any cleaning after the initial flushing process as the sanitization ends after the first flush. The benefit of the embodiments of the present invention which includes the two individually packaged first cup 240 and second cup 250 both having disinfectant-loaded absorbent materials (246,256) is institution of a two-step sanitization that provides additional protection to the patient by including an additional cleaning step using the IPA or scrubbing device to sanitize the hub or connecting interface prior to medication or lock solution administration thereby further preventing potential infections to the patient.

When using the first cup 240, compression of the first absorbent material 246 toward the closed end 242 of the chamber 245 upon connection to the female luer connector or the male luer connector allows the connector to contact the first disinfectant 247 to disinfect the female luer connector or the male luer connector. Similarly, when using the second cup 250, compression of the second absorbent material 256 toward the closed end 252 of the second chamber 255 upon connection to the female luer connector or the male luer connector allows the connector to contact the second disinfectant 257 to disinfect the female luer connector or the male luer connector.

In one or more embodiments, an assembly comprises the device of one or more embodiments connected to a medical connector. In one or more embodiments, the medical connector is selected from a male luer connector, a female luer connector, and needleless connector.

Referring to FIGS. 13-18, the disinfection unit 300 for connection to a medical connector according to an exemplary embodiment of the present disclosure also generally includes a syringe assembly 310 having a syringe barrel 311 having an elongate body 312 defining a chamber 313 for retaining fluid. The syringe barrel 311 includes an open proximal end 314 having a flange 315 and a distal end 316 including a tip 317 having a passageway 318 therethrough in fluid communication with the chamber. The distal end 316 of the barrel also includes a locking luer-type collar 319 concentrically surrounding tip 317. The locking luer-type collar 319 has an internal thread 320. Syringe assembly 310 further includes a stopper 321 connected to an elongate plunger rod 322 having a thumb press 323 at its proximal end and a scrubbing device 330 having a first cup 340 and a second cup 350. A bottom wall 331 spans the first cup 340.

Figure 15:
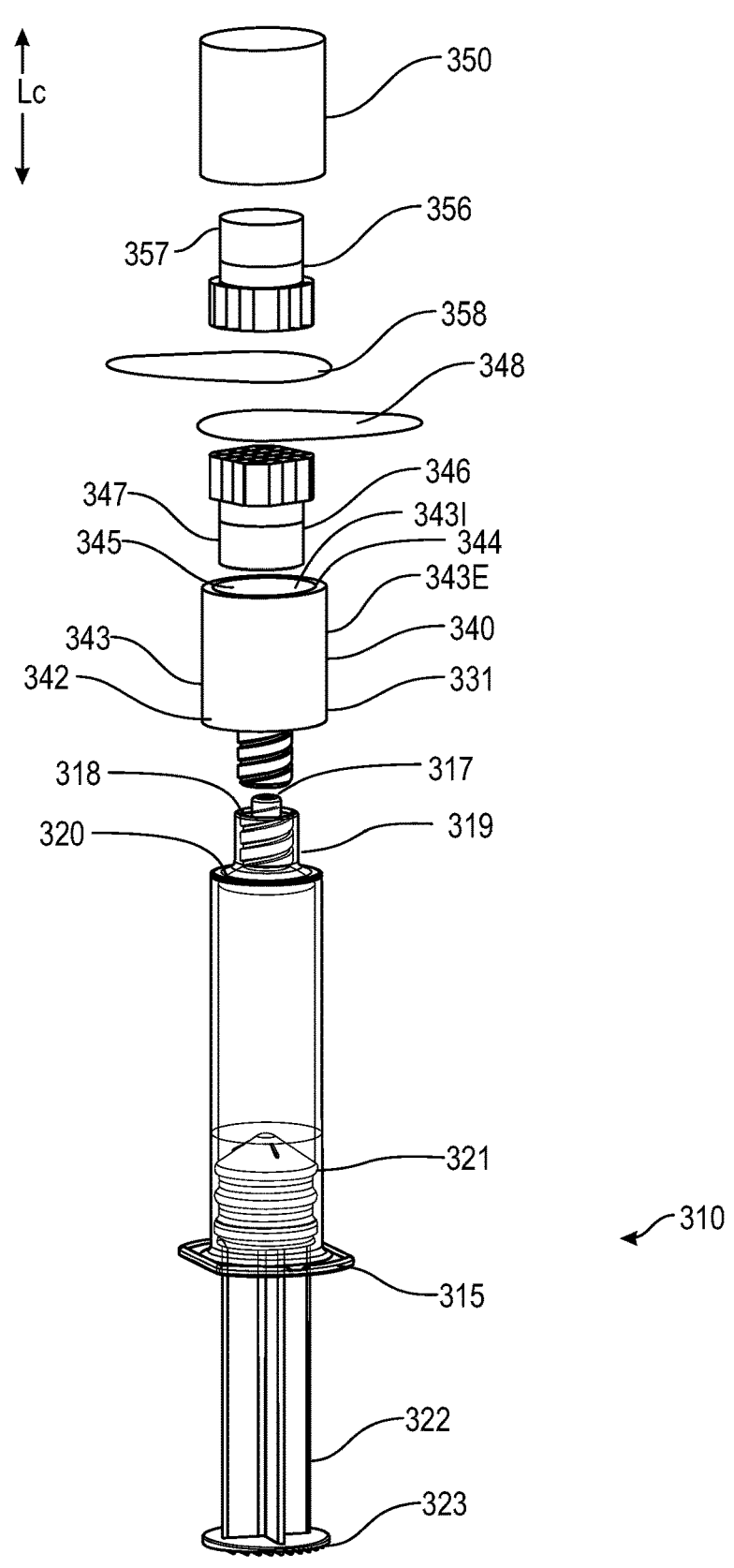
FIG. 15 illustrates an exploded perspective view of a disinfection unit 300 according to an exemplary third embodiment of the disclosure.
Figure 17:
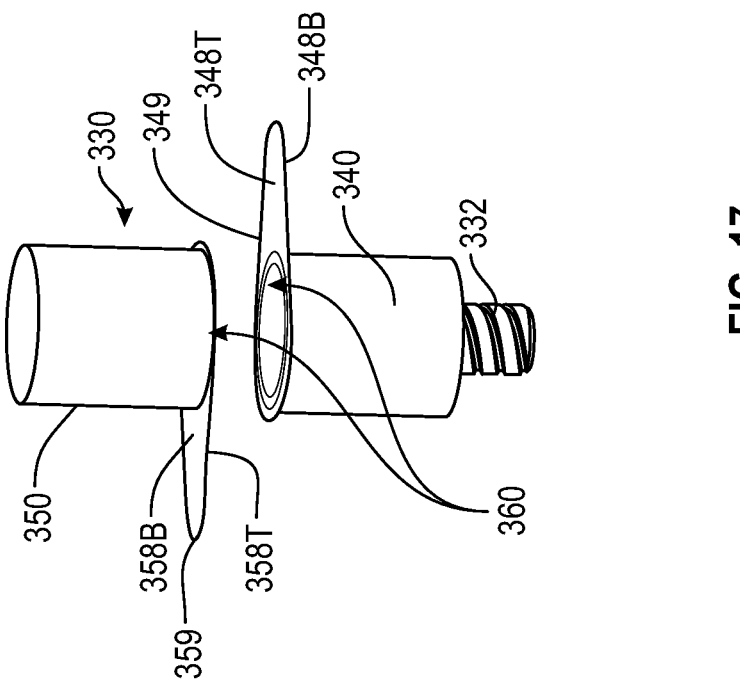
FIG. 17 illustrates a perspective view of the scrubbing element with the second cup detached from the first cup in accordance with an exemplary third embodiment of the disclosure.
Figure 16:
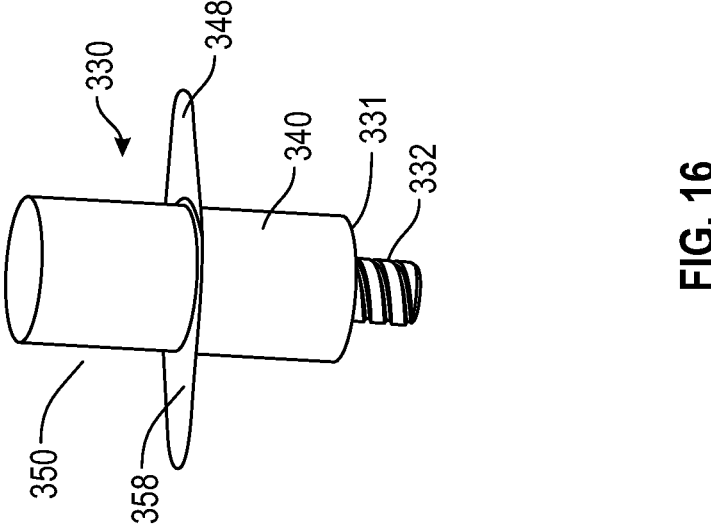
FIG. 16 illustrates a perspective side view of a scrubbing element according to an exemplary third embodiment of the disclosure.

Referring to FIGS. 15-17, the first cup 340 comprises an integral body 341, a closed end 342, an annular wall 343 having a length $L_C$ extending from the closed end 342 to an open end 344 that defines a first chamber 345 containing a first absorbent material 346, a first disinfectant or 347 in the first cup 340, and a first peelable seal 348 having a top web 349. The peelable seal 348 has a bottom surface 348B and a top surface 348T. The first absorbent material 346 is soaked in the first disinfectant 347 or the antimicrobial agent. The open end 344 defines an engagement surface to contact bottom surface 348B of the first peelable seal 348.

Referring to FIGS. 15-17, the second cup 350 comprises an integral body 351, a closed end 352, an annular wall 353 having a length $L_C$ extending from the closed end 352 to an open end 354 that defines a second chamber 355 containing a second absorbent material 356, a second disinfectant 357 in the second cup 350, and a second peelable seal 358 having a top web 359. The second absorbent material 356 is soaked in the second disinfectant 357 or the antimicrobial agent. The open end 354 defines an engagement surface to contact the top surface 358T of the second peelable seal 358.

The open end 344 of the first cup 340 defines an engagement surface to contact bottom surface 348B of the first peelable seal 348 and the open end 354 of the second cup 350 defines an engagement surface to contact the top surface 358T of the second peelable seal 358. The first cup 340 and the second cup 350 are disposed in a top-bottom orientation and the first cup 340 and the second cup 350 in which the top surface of the first peel seal is bonded together with the top surface of the second peel surface using a low bond strength adhesive 360.

Figure 18:
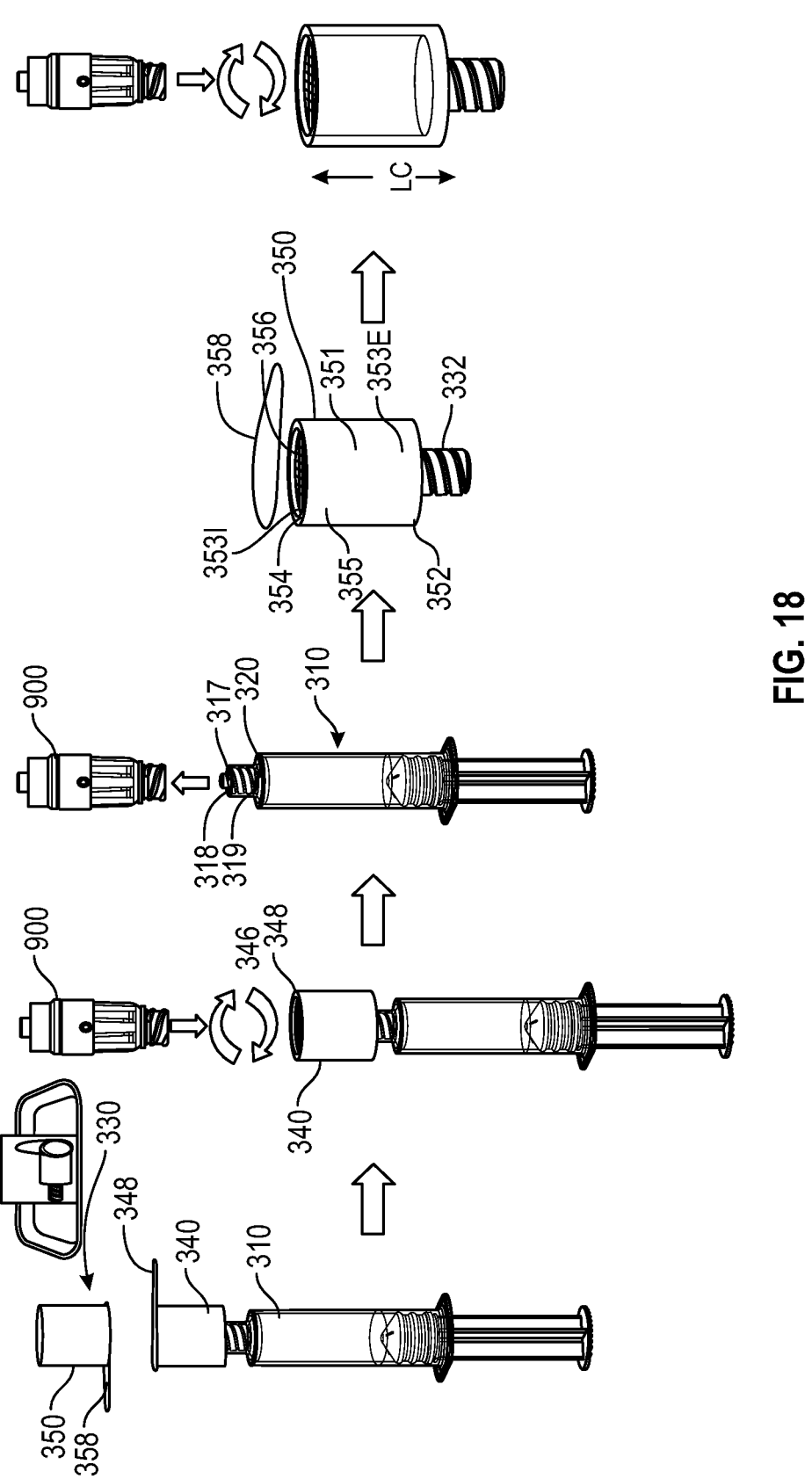
FIG. 18 illustrates a flow chart of a disinfection process using a disinfection unit 200 in accordance with an exemplary third embodiment of the disclosure.

As shown in FIGS. 16-18, syringe assembly 310 can be attached to the first cup 340 of scrubbing device 330 by a mechanical mating features. Once assembled together, the assembly of the syringe assembly 310 and first cup 340 of scrubbing device 330 can withstand, axial, radial, disassembly forces. To remove the first cup 340 of scrubbing device 330 from the syringe barrel, the user shall apply a torque on the entire assembly thus unthreading scrubbing device 330 from the locking luer-type collar 319 at the distal end of barrel to allow attachment of the flush syringe to the IV catheter line. When a torque is applied to either the syringe or first cup 340 of scrubbing device 330 or both, the scrubbing device 330 should unthread off the barrel.

In one or more embodiments shown in FIGS. 16-18, the mechanical mating and assembly features ensure that the device can be assembled in an automated process and ensure device integrity during transport, use, and over the course of the product's shelf life. The assembly of the scrubbing device 330 and collar of the syringe of the present disclosure via a mechanical connection or threaded connection facilitates high speed, automated assembly.

Compared to separate flush syringe and disinfection unit products that are currently available, embodiments of the integrated disinfection unit 300 of the present disclosure provides easy access to the disinfection product at each flush and easier hand operation during disinfection followed by flushing.

In one or more embodiments, the disinfection unit 300 includes a connection element allowing it to be connected to a syringe. In one or more embodiments, the connection element is a threaded connection, for example, luer threaded connection to allow the assembled disinfection unit 300 to be connected to a syringe. In an exemplary implementation of the embodiments of present disclosure, the disinfection unit 300 includes integrated threads or tabs, and other features in any and all combinations allowing the first cup 340 to interface with a threaded fitting of a medical device. In one or more embodiments, the syringe assembly 310 can be attached to the first cup 340 of the scrubbing device 330 using various methods including, but not limited to, mechanical fasteners, snap-fittings, and threaded connection. In one or more embodiments, a threaded connection is disposed on the bottom exterior surface of the disinfection unit 300 having threads that are sized and pitched to engage threads of a luer lock collar on the distal end of the syringe barrel to allow the assembled disinfection unit 300 to be connected to a syringe. In one or more embodiments as shown in FIG. 15, the bottom wall 331 of the first cup 340 of the scrubbing device 330 includes a threaded post 332 disposed in the center of the bottom wall 331 of the first cup 340 that corresponds to the internal thread 320 of the locking luer-type collar 319 on the distal end of the syringe barrel 311.

The scrubbing device 330 can achieve disinfection when used on needle-free connector ("NFC") by integrating a first disinfectant 347 in the first absorbent material 346 disposed and housed in the first chamber 345 of the first cup 340 and a second disinfectant 357 in the second absorbent material 356 disposed and housed in the second chamber 355 of the second cup 350. The first and second disinfectants (347, 357) can be directly included in the first chamber 345 and second chamber 355 and can be absorbed into first absorbent material 346 and into second absorbent material 356 (e.g. sponges or foam material) that fills the chamber of first cup 340 and second cup 350 respectively. The scrubbing device 330 is designed to be compatible in interacting with various disinfectants. In one or more embodiments, the first disinfectant 347 or second disinfectant 357 may include variations of alcohol or chlorhexidine. In one or more embodiments, the first disinfectant 347 or second disinfectant 357 is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorohexidine diacetate, chlorohexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the first disinfectant 347 or second disinfectant 357 comprises at least one of chlorhexidine gluconate and chlorhexidine diacetate. In one or more embodiments, the first disinfectant 347 or second disinfectant 357 is a fluid or a gel.

Figure 14:
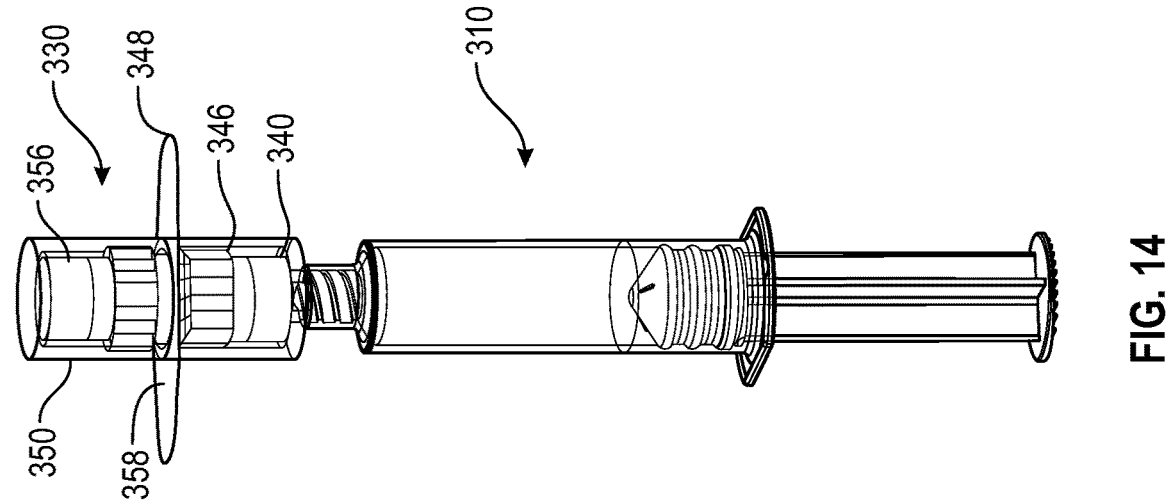
FIG. 14 illustrates a cross-sectional view of a disinfection unit 300 according to an exemplary third embodiment of the disclosure.
Figure 13:
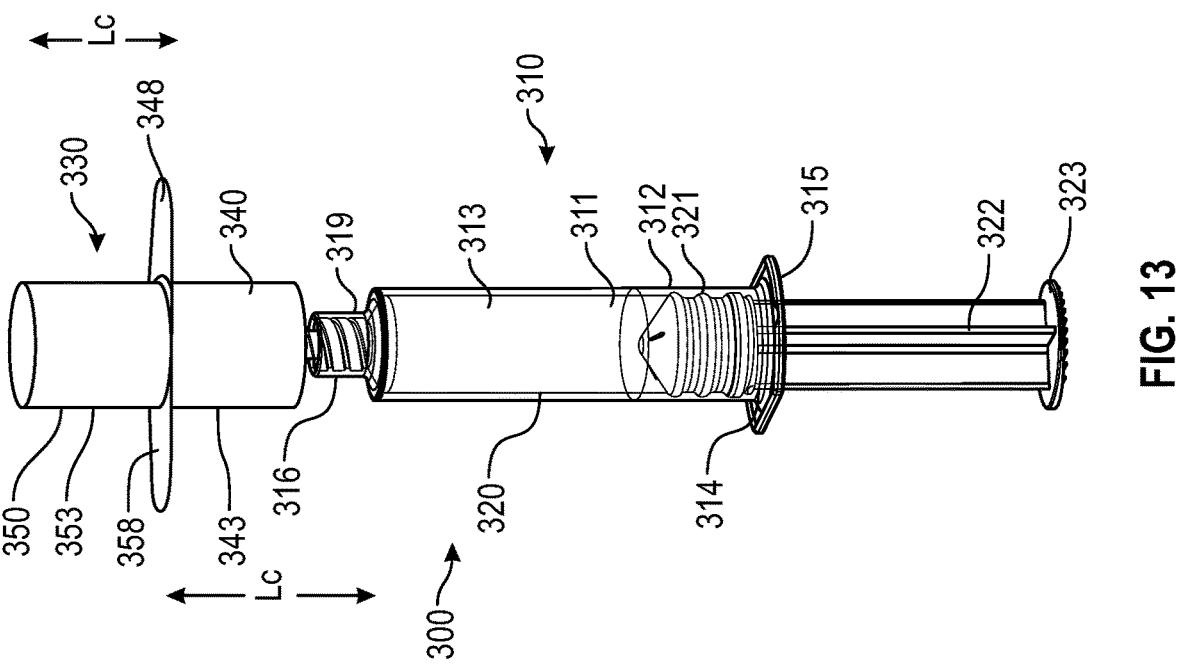
FIG. 13 illustrates a perspective view of a disinfection unit 300 according to an exemplary third embodiment of the disclosure.

First absorbent material 346 soaks up the first disinfectant 347 or the antimicrobial agent that is housed within the first chamber 345 of the first cup 340. In one or more embodiments, the first absorbent material 346 is a nonwoven material, foam, or a sponge. In a specific embodiment, the foam is a polyurethane foam. In a specific embodiment the second absorbent material 356 is in the form of a foam plug. In one or more embodiments, the second absorbent material 356 includes one or more slits as shown in FIGS. 14 and 15.

A first peelable seal 348 having a top web 349 is disposed on the engagement surface of first cup 340 to prevent the first absorbent material 346 from exiting the first chamber 345. With the first absorbent material 346 properly inserted into the first chamber 345 of the first cup 340, the first peelable seal 348 may be secured to the engagement surface of the open end 344 of first cup 340 to seal the scrubbing device 330.

A second peelable seal 358 having a top web 359 is disposed on the engagement surface of second cup 350 to prevent the second absorbent material 356 from exiting the second chamber 355. With the second absorbent material 356 properly inserted into the second chamber 355 of the second cup 350, the second peelable seal 358 may be secured to the engagement surface of the open end 354 of second cup 350 to seal the scrubbing device 330.

Second absorbent material 356 is disposed and housed in the second chamber 355 of the second cup 350 and soaks up the second disinfectant 357 or the antimicrobial agent that is housed within the second chamber 355 of the second cup 350. In one or more embodiments, the second absorbent material 356 is a nonwoven material, foam, or a sponge. In a specific embodiment, the foam is a polyurethane foam. In a specific embodiment the second absorbent material 356 is in the form of a foam plug. In one or more embodiments, the second absorbent material 356 includes one or more slits as shown in FIGS. 14 and 15.

The first peelable seal 348 and second peelable seal 358 minimize entry of potential particulate hazard and also provides a substantially impermeable enclosure for the scrubbing device 330, provides a leak prevention and protection enclosure, protects the contents of first absorbent material 346 and second absorbent material 356 contained within the first chamber 345 and second chamber 355, respectively and/or maintains a sealed, sterilized environment. The first peelable seal 348 and second peelable seal 358 provide a sufficient seal at a range of temperatures, pressures, and humidity levels. The first peelable seal 348 and second peelable seal 358 may be disposed on the respective open ends (344, 354) of the first cup 340 and second cup 350 to prevent the pre-filled first and second disinfectants (347, 357) from exiting the chamber of the respective first cup 340 and second cup 350.

The first peelable seal 348 and second peelable seal 358 can be a plastic sealed aluminum, and can be chemically-resistant, light-blocking, non-permeable, or sterile In one or more embodiments, the first peelable seal 348 and second peelable seal 358 comprises an aluminum or multi-layer polymer film peel back top. In a specific embodiment, the first peelable seal 348 and second peelable seal 358 is heat-sealed or induction sealed to the engagement surface of the open end (344, 354) of cup (340,350) to seal the scrubbing device 330. In one or more embodiments, the first peelable seal 348 and second peelable seal 358 comprises a moisture barrier.

The first absorbent material 346 and second absorbent material 356 and the disinfectant or the antimicrobial agent contacts the male luer connector, the female luer connector, and the hemodialysis connector after insertion of the connector into the open end (344, 354) of the respective cups 340 and 350.

In one or more embodiments, the female connector may be selected from the group consisting essentially of needle-free connectors, catheter luer connectors, stopcocks, and hemodialysis connectors. In one or more embodiments, the male connector may be an intravenous tubing end, a stopcock or male lock luer.

The first cup 340 and the second cup 350 are made from any type of plastic materials such as polycarbonate, polypropylene, polyethylene, polyethylene terephthalate, polylactide, acrylonitrile butadiene styrene or any other moldable plastic material used in medical devices. In one or more embodiments, the first cup 340 and the second cup 350 comprises a polypropylene or polyethylene material.

To avoid having to use different types of disinfecting caps to clean different types of connectors, disinfection device 300 with first cup 340 and second cup 350 is compatible and engages with male luer connectors and also with female luer connectors thereby allowing the user to clean different types of connectors with a single device. Upon mounting the first cup 340 and second cup 350 onto female luer connectors, or a male luer connector, the female or male medical connector engage the interior wall upon insertion into the first chamber 345 or second chamber 355 and contact the first absorbent material 346 and into second absorbent material 356 soaked with disinfectant or the antimicrobial agent. Hence, the device of the present disclosure can disinfect both male and female luer connectors, thus fulfilling a current need in the art.

Other aspects of the present disclosure are directed to methods of disinfecting medical connectors and assemblies. In one or more embodiments, a method of disinfecting a medical connector comprises connecting the device of one or more embodiments to a medical connector, wherein connecting includes frictionally engaging the interior wall surface upon insertion into the chamber such that the medical connector contacts the absorbent material and the disinfectant or antimicrobial agent.

In use, a clinician peels the second cup 350 off the first cup to remove the second cup from the scrubbing device 330 in a manner that the first peelable seal 348 remains on the first cup 340 and the second peelable seal 358 remains on the second cup 350. The bond strength of the first peelable seal 348 to the first cup 340 and the bond strength of the second peelable seal 358 to the second cup 350 is greater than the bond strength of the low bond strength adhesion that bonds the top surface of the first peel seal together with the top surface of the second peel surface thus allowing the second cup to be removed from the first cup 340 while allowing the first peelable seal 348 remains on the first cup 340 and the second peelable seal 358 remains on the second cup 350. The clinician places the second cup 350 on a sterile tray for subsequent use of the sealed second cup. The clinician peels the top web 349 of the first peelable seal 348 from the first cup 40. The clinician then disinfects the NFC using the first cup 340 before flushing an IV line. Upon insertion of the NFC into the first cup 340, the first absorbent material 346 soaked with first disinfectant 347 contacts the NFC. Next, the clinician removes first cup 340 of the scrubbing device 330 from the syringe barrel, by applying a torque on the entire assembly thus unthreading scrubbing device 330 from the locking luer-type collar 319 at the distal end of syringe barrel 311 to allow attachment of the flush syringe to the IV catheter line to flush the IV line. When a torque is applied to either the syringe or first cup 340 or both, the first cup 340 of the scrubbing device 330 should unthread off the barrel. The clinician then engages the threads of the luer lock collar on the distal end of the syringe barrel to the NFC to connect the NFC to the flush syringe. After flushing, the clinician picks up detached second cup 350 of scrubbing device 330 and peels top web 359 from second cup 350 after flushing IV line to expose the second absorbent material 356 soaked in the second disinfectant 357 and disinfects the NFC using the second cup 350 by contacting the male luer connector, the female luer connector, and the hemodialysis connector after insertion of the NFC connector into second cup 350 with second absorbent material 356 soaked in the second disinfectant 357. As in current practice, the clinician then administers medicine and performs a second flush of the IV line using a Flush syringe to remove any medication left in your catheter and scrubs the hub using a disinfecting wipe or scrubbing device. The clinician then "locks" the IV line using a lock syringe filled with a heparin flush to help prevent blood clots from forming in the catheter. Finally, a new disinfecting cap is attached to the dwelling catheter hub.

As noted above, currently products and SASH practice does not address any cleaning after the initial flushing process as the sanitization ends after the first flush. The benefit of the embodiments of the present invention which includes the two individually packaged first cup 340 and second cup 350 both having disinfectant-loaded absorbent materials (346,356) is institution of a two-step sanitization that provides additional protection to the patient by including an additional cleaning step using the IPA or scrubbing device to sanitize the hub or connecting interface prior to medication or lock solution administration thereby further preventing potential infections to the patient.

When using the first cup 340, compression of the first absorbent material 346 toward the closed end 342 of the first chamber 345 upon connection to the female luer connector or the male luer connector allows the connector to contact the first disinfectant 347 to disinfect the female luer connector or the male luer connector. Similarly, when using the second cup 350, compression of the second absorbent material 356 toward the closed end 352 of the second chamber 355 upon connection to the female luer connector or the male luer connector allows the connector to contact the second disinfectant 357 to disinfect the female luer connector or the male luer connector.

In one or more embodiments, an assembly comprises the device of one or more embodiments connected to a medical connector. In one or more embodiments, the medical connector is selected from a male luer connector, a female luer connector, and needleless connector.

Referring to FIGS. 19-23, the disinfection unit 400 for connection to a medical connector according to an exemplary embodiment of the present disclosure also generally includes a syringe assembly 410 having a syringe barrel 411 having an elongate body 412 defining a chamber 413 for retaining fluid. The syringe barrel 411 includes an open proximal end 414 having a flange 415 and a distal end 416 including a tip 417 having a passageway 418 therethrough in fluid communication with the chamber. The distal end 416 of the barrel also includes a locking luer-type collar 419 concentrically surrounding tip 417. The locking luer-type collar 419 has an internal thread 420. Syringe assembly 410 further includes a stopper 421 connected to an elongate plunger rod 422 having a thumb press 423 at its proximal end, and a scrubbing device 430 having a first cup 440 and a second cup 450. A bottom wall 431 spans the first cup 440.

Figure 22:
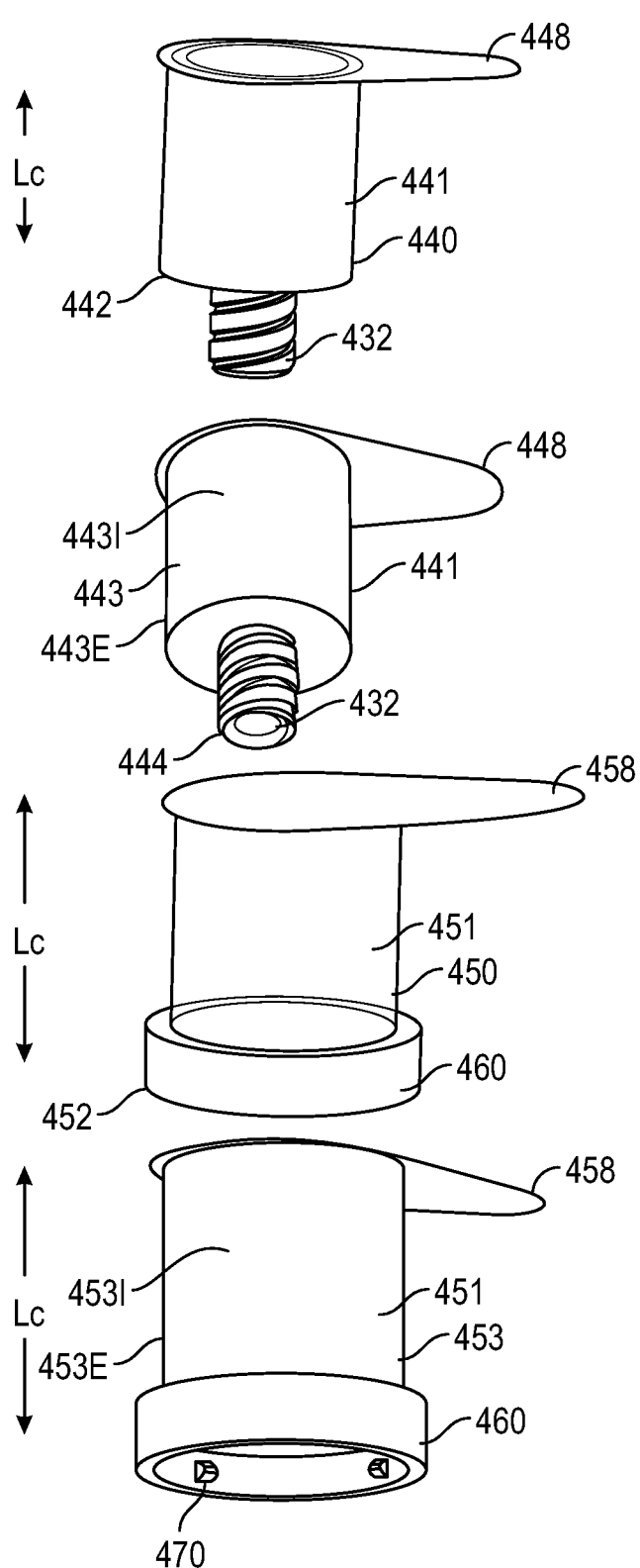
FIG. 22 illustrates perspective side views of the first and second cups of a scrubbing element according to an exemplary fourth embodiment of the disclosure.

Referring to FIG. 22, the first cup 440 comprises an integral body 441, a closed end 442, an annular wall 443 having a length $L_C$ extending from the closed end 442 to an open end 444 that defines a first chamber 445 containing a first absorbent material 446, a first disinfectant 447 in the first cup 440, and a first peelable seal 448 having a top web 449. The peelable seal 448 has a bottom surface 448B and a top surface 448T. The first absorbent material 446 is soaked in the first disinfectant 447 or the antimicrobial agent. The open end 444 defines an engagement surface to contact bottom surface 448B of the first peelable seal 448.

The open end 444 of the first cup 440 defines an engagement surface to contact bottom surface 448B of the first peelable seal 448 and the open end 454 of the second cup 450 defines an engagement surface to contact the top surface 458T of the second peelable seal 458.

Figure 23:
FIG. 23 illustrates a flow chart of a disinfection process using a disinfection unit 400 in accordance with an exemplary fourth embodiment of the disclosure.
Figure 25:
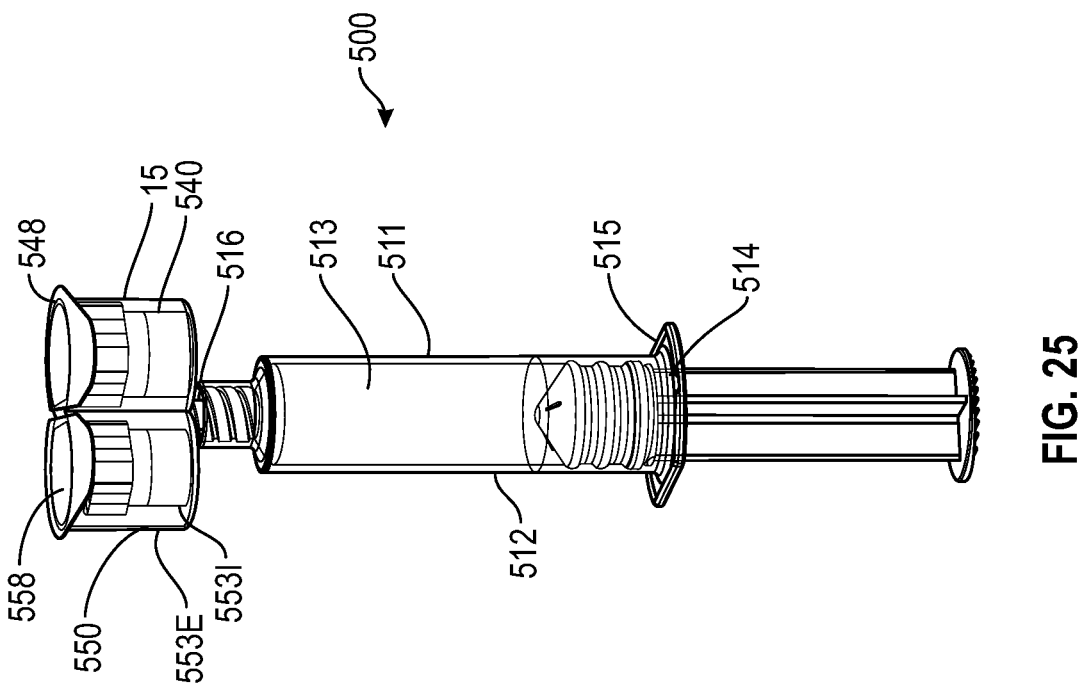
FIG. 25 illustrates a cross-sectional view of a disinfection unit 500 according to an exemplary fifth embodiment of the disclosure.
Figure 24:
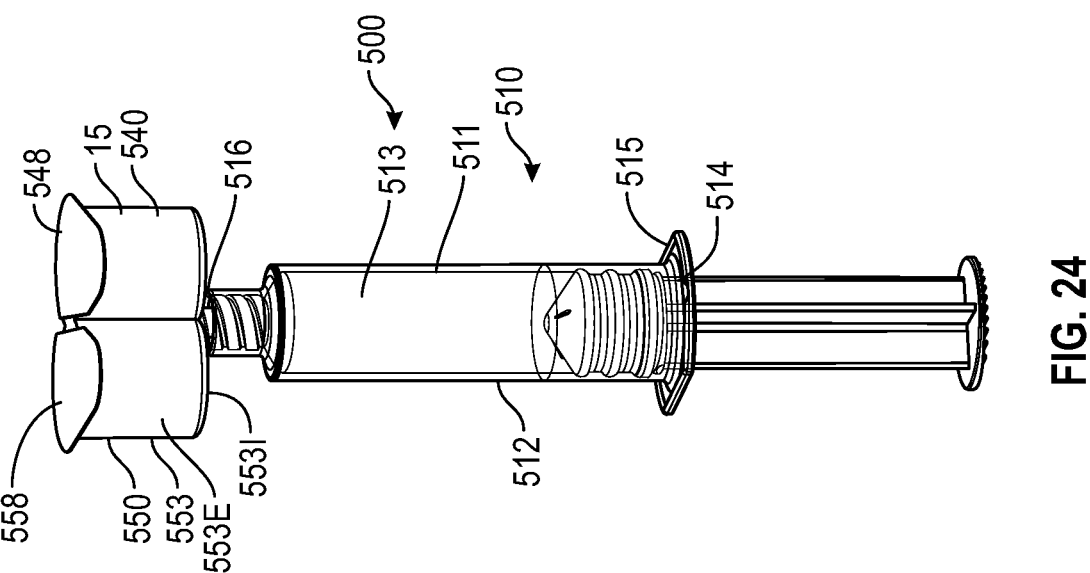
FIG. 24 illustrates a perspective view of a disinfection unit 500 according to an exemplary fifth embodiment of the disclosure.

As shown in FIG. 23, syringe assembly 410 can be attached to the first cup 440 of scrubbing device 430 by a mechanical mating features. Once assembled together, the assembly of the syringe assembly 410 and first cup 440 of scrubbing device 430 can withstand, axial, radial, disassembly forces. To remove the first cup 440 of scrubbing device 430 from the syringe barrel, the user shall apply a torque on the entire assembly thus unthreading scrubbing device 430 from the locking luer-type collar 419 at the distal end of barrel to allow attachment of the flush syringe to the IV catheter line. When a torque is applied to either the syringe or first cup 440 of scrubbing device 430 or both, the scrubbing device 430 should unthread off the barrel.

Referring to FIG. 22, the second cup 450 comprises an integral body 451, a closed end 452, an annular wall 453 having a length L$_C$ extending from the closed end 452 to an open end 454 that defines a second chamber 455 containing a second absorbent material 456, the closed end 452 of the annular wall 453 having a ledge extending from the closed end 452, a second disinfectant 457 in the second cup 450, and a second peelable seal 458 having a top web 459. The second absorbent material 456 is soaked in the second disinfectant 457 or the antimicrobial agent. The open end 454 defines an engagement surface to contact the top surface 448T of the second peelable seal 458.

As shown in FIGS. 20-23, the second cup and the syringe assembly are interlocked through interference fit or snap fit of the thumb press of the syringe and ledge of the second cup. A ledge/wedge portions can be arranged at the closed end of the annular wall of the second cup to provide for a snap on connection to the thumb press. The inner surface of the top wall disposed at the closed end of the annular wall of the second cup may have a recess into which the ledge/wedge of the insert may be inserted.

In one or more embodiments shown in FIGS. 20-23, the mechanical mating and assembly features ensure that the device can be assembled in an automated process and ensure device integrity during transport, use, and over the course of the product's shelf life. The assembly of the scrubbing device 430 and collar of the syringe of the present disclosure via a mechanical connection or threaded connection facilitates high speed, automated assembly.

Compared to separate flush syringe and disinfection unit products that are currently available, embodiments of the integrated disinfection unit 400 of the present disclosure provides easy access to the disinfection product at each flush and easier hand operation during disinfection followed by flushing.

Figure 21:
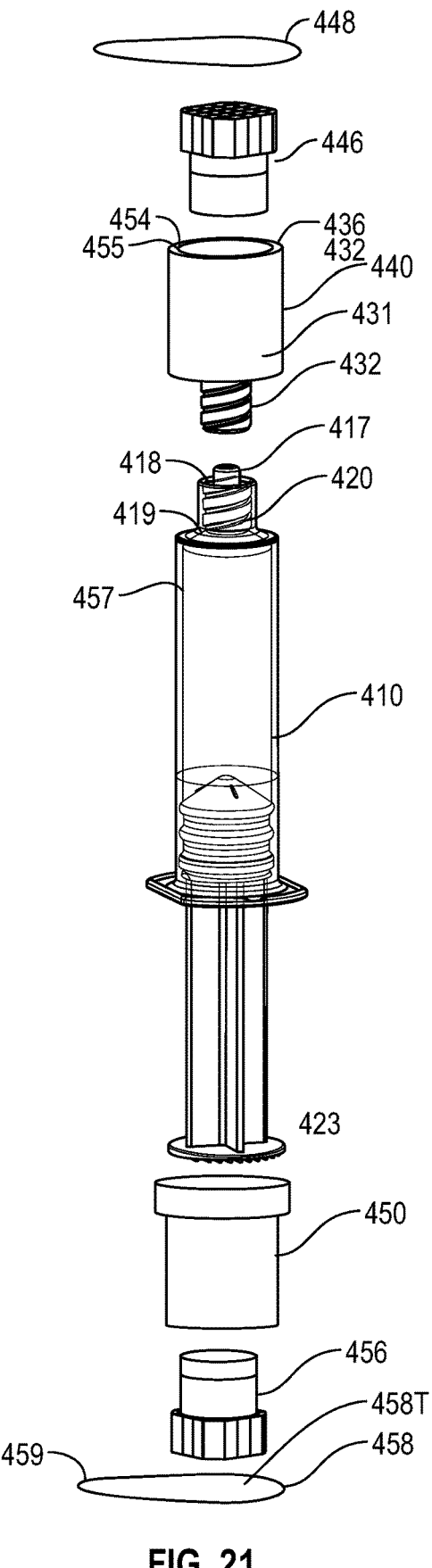
FIG. 21 illustrates an exploded perspective view of a disinfection unit 400 according to an exemplary fourth embodiment of the disclosure.

In one or more embodiments, the disinfection unit 400 includes a connection element allowing it to be connected to a syringe. In one or more embodiments, the connection element is a threaded connection, for example, luer threaded connection to allow the assembled disinfection unit 400 to be connected to a syringe. In an exemplary implementation of the embodiments of present disclosure, the disinfection unit 400 includes integrated threads or tabs, and other features in any and all combinations allowing the first cup 440 to interface with a threaded fitting of a medical device. In one or more embodiments, the syringe assembly 410 can be attached to the first cup 440 of the scrubbing device 430 using various methods including, but not limited to, mechanical fasteners, snap-fittings, and threaded connection. In one or more embodiments, a threaded connection is disposed on the bottom exterior surface of the first cup of the disinfection unit 400 having threads that are sized and pitched to engage threads of a luer lock collar on the distal end of the syringe barrel to allow the assembled disinfection unit 400 to be connected to a syringe. In one or more embodiments as shown in FIG. 21, the bottom wall 431 of the first cup 440 of the scrubbing device 430 includes a threaded post 432 disposed in the center of the bottom wall

431 of the first cup 440 that corresponds to the internal thread 420 of the locking luer-type collar 419 on the distal end of the syringe barrel 411. As shown in FIG. 23, the second cup and the syringe assembly are interlocked through interference fit or snap fit of the thumb press of the syringe and ledge of the second cup. A ledge/wedge portions can be arranged at the closed end of the annular wall of the second cup to provide for a snap on connection to the thumb press. The inner surface of the top wall disposed at the closed end of the annular wall of the second cup may have a recess into which the peripheral ledge 460 of the insert may be inserted.

The closed end defines an end face that includes a peripheral ledge 460 extending radially outward from the annular wall.

The second cup is adapted to be snap fit over the thumb press of the plunger rod, opposite of a luer tip. Referring to FIG. 23, in one or more embodiments, the second cup may be connected to the thumb press with a rim disposed on the peripheral ledge and radially inward to create a lip or rim. An interior surface of the peripheral ledge in the interior annular wall surface of the second cup at the closed end includes at least two or more mating protrusions 470 which allow the thumb press to mate together with the second cup via a snap fit connection. In one or more embodiments, the snap fit connection comprises a protruding edge and a snap-in area. The protruding edge may be disposed on an interior surface of the peripheral sidewall of the peripheral ledge or the interior annular wall surface of the second cup at the closed end, and the corresponding snap-in area is disposed on the opposite surface as the protruding edge to allow the protruding edge and snap-in area to interlock.

In one or more embodiments, mechanical locking is achieved by use of protrusions, ribs, undercuts, interference fits, and locking tapers. In certain embodiments of the integrated second cup 450 with the thumb press of the present disclosure, the interior annular wall surface of the second cup 450 at the closed end having locking tabs 470, the locking tabs 470 are annular and structurally more robust and are easier to mold.

In one or more embodiments, the clips are configured as a locking mechanism whereby one-way flexing clips which require relatively low axial forces to assemble and produce significant locking strength. As the second cup and the thumb press are assembled, the clips flex inward until they enter the thumb press of the plunger rod. Once contact between the clips and thumb press is made, the clips spring or deflect outward creating a mate between the thumb press and second cup 450.

Specifically, during assembly of the second cup 450 and the thumb press 423, the closed end of the second cup 450 is inserted into the thumb press 423. The clips flex inward towards the annular wall of the second cup 450. Once the clips move past and clear the thumb press 423, the clips spring outward creating a permanent mate between the two parts without the use of adhesives. Once the assembly is complete, the mechanical mating prevents the second cup 450 from being removed from the thumb press 423 by pulling the components away from each other.

As the second cup and thumb press are assembled, bottom end of the cup is oriented to face the top end of the thumb press. During assembly, the second cup is pressed onto the thumb press, the peripheral rim causes the protrusions on the interior annular wall surface of the second cup 450 at the closed end to radiate outwards. Once the protrusions of the cup clear the peripheral rim of the thumb press, the protrusions snap back inward and lock the cup onto the thumb press.

The second cup may also comprises a skirt that extend away from the closed end of the second cup 450. The skirt comprises of a lip that is situated on the side wall of the skirt facing towards the x-axis of the second cup. In general, as the cup and the thumb press are assembled, the outer skirt of the second cup flex outward until they engage a beveled rim on the exterior wall surface on the thumb press. Once the lip clear the beveled rim, the outer skirt springs inward-creating a lock between the thumb press and the second cup.

The scrubbing device 430 can achieve disinfection when used on needle-free connector ("NFC") by integrating a first disinfectant 447 in the first absorbent material 446 disposed and housed in the first chamber 445 of the first cup 440 and a second disinfectant 457 in the second absorbent material 456 disposed and housed in the second chamber 455 of the second cup 450. The first and second disinfectants (447, 457) can be directly included in the first chamber 445 and second chamber 455 and can be absorbed into first absorbent material 446 and into second absorbent material 456 (e.g. sponges or foam material) that fills the chamber of first cup 440 and second cup 450 respectively. The scrubbing device 430 is designed to be compatible in interacting with various disinfectants. In one or more embodiments, the first disinfectant 447 or second disinfectant 457 may include variations of alcohol or chlorhexidine. In one or more embodiments, the first disinfectant 447 or second disinfectant 457 is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butylhydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the first disinfectant 447 or second disinfectant 457 comprises at least one of chlorhexidine gluconate and chlorhexidine diacetate. In one or more embodiments, the first disinfectant 447 or second disinfectant 457 is a fluid or a gel.

First absorbent material 446 soaks up the first disinfectant 447 that is housed within the first chamber 445 of the first cup 440. In one or more embodiments, the first absorbent material 446 is a nonwoven material, foam, or a sponge. In a specific embodiment, the foam is a polyurethane foam. In a specific embodiment the second absorbent material 456 is in the form of a foam plug. In one or more embodiments, the second absorbent material 456 includes one or more slits as shown in FIGS. 21 and 23.

A first peelable seal 448 having a top web 449 is disposed on the engagement surface of first cup 440 to prevent the first absorbent material 446 from exiting the first chamber 445. With the first absorbent material 446 properly inserted into the first chamber 445 of the first cup 440, the first peelable seal 448 may be secured to the engagement surface of the open end 444 of first cup 440 to seal the scrubbing device 430.

A second peelable seal 458 having a top web 459 is disposed on the engagement surface of second cup 450 to prevent the second absorbent material 456 from exiting the second chamber 455. With the second absorbent material 456 properly inserted into the second chamber 455 of the second cup 450, the second peelable seal 458 may be secured to the engagement surface of the open end 454 of second cup 450 to seal the scrubbing device 430.

Second absorbent material 456 is disposed and housed in the second chamber 455 of the second cup 450 and soaks up the second disinfectant 457 that is housed within the second chamber 455 of the second cup 450. In one or more embodiments, the second absorbent material 456 is a nonwoven material, foam, or a sponge. In a specific embodiment, the foam is a polyurethane foam. In a specific embodiment the second absorbent material 456 is in the form of a foam plug. In one or more embodiments, the second absorbent material 456 includes one or more slits as shown in FIGS. 21 and 23.

The first peelable seal 448 and second peelable seal 458 minimize entry of potential particulate hazard and also provides a substantially impermeable enclosure for the scrubbing device 430, provides a leak prevention and protection enclosure, protects the contents of first absorbent material 446 and second absorbent material 456 contained within the first chamber 445 and second chamber 455, respectively and/or maintains a sealed, sterilized environment. The first peelable seal 448 and second peelable seal 458 provide a sufficient seal at a range of temperatures, pressures, and humidity levels. The first peelable seal 448 and second peelable seal 458 may be disposed on the respective open ends (444, 454) of the first cup 440 and second cup 450 to prevent the pre-filled first and second disinfectants (447, 457) from exiting the chamber of the respective first cup 440 and second cup 450.

The first peelable seal 448 and second peelable seal 458 can be a plastic sealed aluminum, and can be chemically-resistant, light-blocking, non-permeable, or sterile In one or more embodiments, the first peelable seal 448 and second peelable seal 458 comprises an aluminum or multi-layer polymer film peel back top. In a specific embodiment, the first peelable seal 448 and second peelable seal 458 is heat-sealed or induction sealed to the engagement surface of the open end (444, 454) of cup (440,450) to seal the scrubbing device 430. In one or more embodiments, the first peelable seal 448 and second peelable seal 458 comprises a moisture barrier.

The first absorbent material 446 and second absorbent material 456 and the disinfectant contacts the male luer connector, the female luer connector, and the hemodialysis connector after insertion of the connector into the open end (444, 454) of the respective cups 440 and 450.

In one or more embodiments, the female connector may be selected from the group consisting essentially of needle-free connectors, catheter luer connectors, stopcocks, and hemodialysis connectors. In one or more embodiments, the male connector may be an intravenous tubing end, a stopcock or male lock luer.

The first cup 440 and the second cup 450 are made from any type of plastic materials such as polycarbonate, polypropylene, polyethylene, polyethylene terephthalate, polylactide, acrylonitrile butadiene styrene or any other moldable plastic material used in medical devices. In one or more embodiments, the first cup 440 and the second cup 450 comprises a polypropylene or polyethylene material.

To avoid having to use different types of disinfecting caps to clean different types of connectors, disinfection device 400 with first cup 440 and second cup 450 is compatible and engages with male luer connectors and also with female luer connectors thereby allowing the user to clean different types of connectors with a single device. Upon mounting the first cup 440 and second cup 450 onto female luer connectors, or a male luer connector, the female or male medical connector engage the interior wall upon insertion into either chambers 445 or 455 and contact the first absorbent material 446 and into second absorbent material 456 soaked with disinfectant.

Hence, the device of the present disclosure can disinfect both male and female luer connectors, thus fulfilling a current need in the art.

Other aspects of the present disclosure are directed to methods of disinfecting medical connectors and assemblies. In one or more embodiments, a method of disinfecting a medical connector comprises connecting the device of one or more embodiments to a medical connector, wherein connecting includes frictionally engaging the interior wall surface upon insertion into the chamber such that the medical connector contacts the absorbent material and the disinfectant.

In use, a clinician snaps off and removes the second cup from the syringe assembly and the clinician places the second cup 450 on a sterile tray for subsequent use of the sealed second cup for disinfection of NFC before flushing. As discussed above, snap features in the underside of second cup separates from the thumb press of the plunger of the syringe. The clinician peels the top web 449 of the first peelable seal 448 from the first cup 40. The clinician then disinfects the NFC using the first cup 440 before flushing an IV line. Upon insertion of the NFC into the first cup 440, the first absorbent material 446 soaked with disinfectant 447 contacts the NFC. Next, the clinician removes first cup 440 of the scrubbing device 430 from the syringe barrel, by applying a torque on the entire assembly thus unthreading scrubbing device 430 from the locking luer-type collar 419 at the distal end of syringe barrel 411 to allow attachment of the flush syringe to the IV catheter line to flush the IV line. When a torque is applied to either the syringe or first cup 440 or both, the first cup 440 of the scrubbing device 430 should unthread off the barrel. The clinician then engages the threads of the luer lock collar on the distal end of the syringe barrel to the NFC to connect the NFC to the flush syringe. After flushing, the clinician picks up detached second cup 450 of scrubbing device 430 and peels top web 459 from second cup 450 after flushing IV line to expose the second absorbent material 456 soaked in the second disinfectant 457 and disinfects the NFC using the second cup 450 by contacting the male luer connector, the female luer connector, and the hemodialysis connector after insertion of the NFC connector into second cup 450 with second absorbent material 456 soaked in the second disinfectant 457. As in current practice, the clinician then administers medicine and performs a second flush of the IV line using a Flush syringe to remove any medication left in your catheter and scrubs the hub using a disinfecting wipe or scrubbing device. The clinician then "locks" the IV line using a lock syringe filled with a heparin flush to help prevent blood clots from forming in the catheter. Finally, a new disinfecting cap is attached to the dwelling catheter hub.

As noted above, currently products and SASH practice does not address any cleaning after the initial flushing process as the sanitization ends after the first flush. The benefit of the embodiments of the present invention which includes the two individually packaged first cup 440 and second cup 450 both having disinfectant-loaded absorbent materials (446,456) is institution of a two-step sanitization that provides additional protection to the patient by including an additional cleaning step using the IPA or scrubbing device to sanitize the hub or connecting interface prior to medication or lock solution administration thereby further preventing potential infections to the patient.

When using the first cup 440, compression of the first absorbent material 446 toward the closed end 442 of the first chamber 445 upon connection to the female luer connector or the male luer connector allows the connector to contact the first disinfectant 447 to disinfect the female luer connector or the male luer connector. Similarly, when using the second cup 450, compression of the second absorbent material 456 toward the closed end 452 of the second chamber 455 upon connection to the female luer connector or the male luer connector allows the connector to contact the second disinfectant 457 to disinfect the female luer connector or the male luer connector.

In one or more embodiments, an assembly comprises the device of one or more embodiments connected to a medical connector. In one or more embodiments, the medical connector is selected from a male luer connector, a female luer connector, and needleless connector.

In another alternate embodiment, referring to FIGS. 24-29, a disinfection unit 500 for connection to a medical connector includes a syringe assembly 510 having a syringe barrel 511 having an elongate body 512 defining a chamber 513 for retaining fluid. The syringe barrel 511 includes an open proximal end 514 having a flange 515 and a distal end 516 including a tip 517 having a passageway 518 therethrough in fluid communication with the chamber. The distal end 516 of the barrel also includes a locking luer-type collar 519 concentrically surrounding tip 517. The locking luer-type collar 519 has an internal thread 520. Syringe assembly 510 further includes a stopper 521 connected to an elongate plunger rod 522 having a thumb press 523 at its proximal end.

Referring to FIGS. 24-29, the disinfection unit 500 for connection to a medical connector according to an exemplary embodiment of the present disclosure also generally includes a scrubbing device 530 having a first cup 540 and a second cup 550. A bottom wall 531 spans the first cup 540 and a second cup 550.

Referring to FIGS. 24-29, the first cup 540 comprises an integral body 541, a closed end 542, an annular wall 543 having a length $L_C$ extending from the closed end 542 to an open end 544 that defines a first chamber 545 containing a first absorbent material 546, a first disinfectant 547 in the first cup 540, and a first peelable seal 548. The first absorbent material 546 is soaked in the first disinfectant 547. The open end 544 defines an engagement surface to contact the first peelable seal 548 having a top web 549.

Referring to FIGS. 24-29, the second cup 550 comprises an integral body 551, a closed end 552, an annular wall 553 having a length $L_C$ extending from the closed end 552 to an open end 554 that defines a chamber 555 containing a second absorbent material 556, a second disinfectant 557 in the second cup 550, and a second peelable seal 558 having a top web 559. The second absorbent material 556 is soaked in the second disinfectant 557. The open end 554 defines an engagement surface to contact the second peelable seal 558.

The first cup 540 and the second cup 550 are disposed in a side-by-side orientation and the first cup 540 and the second cup 550 are bounded a female T-slot 570 feature on the first cup 540 that engages with a male T-nut fastener 580 on the second cup 550. In an alternate embodiment, the first cup 540 and the second cup 550 are bounded a female T-slot 570 feature on the second cup 550 that engages with a male T-nut fastener 580 on the first cup 540. Detents on the T-slot and T-nut fastener provide a mechanical lock between the two components. Once the t-slot may be mounted with a corresponding t-nut fastener having an elliptical shoulder which, with a 90° turn, aligns within the upper portion of the t-slot & locks into the t-slot with a strong connection. To remove the first cup 540 from the syringe barrel, the user shall apply an axial force to either to the bottom of the first cup in an upward direction toward the user or grab and pull the top portion of the first cup or both toward the user to disengage the first cup of the scrubbing device 530 from the second cup of the scrubbing device 530. To remove the second cup of the scrubbing device 530 from the syringe barrel, the user shall apply a torque on the entire assembly thus unthreading scrubbing device 530 from the locking luer-type collar 519 at the distal end of barrel to allow attachment of the flush syringe to the IV catheter line. When a torque is applied to either the syringe or scrubbing device 530 or both, the scrubbing device 530 should unthread off the barrel.

As shown in FIGS. 26-29, syringe assembly 510 can be attached to scrubbing device 330 having mechanical mating features. Once assembled together, the assembly of the syringe assembly 510 and scrubbing device 530 can withstand, axial, radial, disassembly forces. To remove the scrubbing device 530 from the syringe barrel, the user shall apply a torque on the entire assembly thus unthreading scrubbing device 530 from the locking luer-type collar 519 at the distal end of barrel to allow attachment of the flush syringe to the IV catheter line. When a torque is applied to either the syringe or scrubbing device 530 or both, the scrubbing device 530 should unthread off the barrel.

In the prior art, a "cradle" underside is employed under where the disinfecting unit is held resulting in the cradle being easily disassembled by a user during normal use. The assembly of the scrubbing device 530 and collar of the syringe of the present disclosure does not require a separate "cradle" or other device to assemble the devices together.

In one or more embodiments as shown in FIGS. 26-29, the mechanical mating and assembly features ensure that the device can be assembled in an automated process and ensure device integrity during transport, use, and over the course of the product's shelf life. The assembly of the scrubbing device 530 and collar of the syringe of the present disclosure via a mechanical connection or threaded connection facilitates high speed, automated assembly.

Compared to separate flush syringe and disinfection unit products that are currently available, embodiments of the integrated disinfection unit of the present disclosure provides easy access to the disinfection product at each flush and easier hand operation during disinfection followed by flushing.

In one or more embodiments, shown in FIGS. 26-29. the disinfection unit 500 includes a connection element allowing it to be connected to a syringe. In one or more embodiments, the connection element is a threaded connection, for example, luer threaded connection to allow the assembled disinfection unit 500 to be connected to a syringe. In an exemplary implementation of the embodiments of present disclosure, the disinfection unit 500 includes integrated threads or tabs, and other features in any and all combinations allowing it to interface with a threaded fitting of a medical device. In one or more embodiments, the syringe assembly 510 can be attached to scrubbing device 530 using various methods including, but not limited to, mechanical fasteners, snap-fittings, and threaded connection. In one or more embodiments, a threaded connection is disposed on the bottom exterior surface of the disinfection unit 500 having threads that are sized and pitched to engage threads of a luer lock collar on the distal end of the syringe barrel to allow the assembled disinfection unit 500 to be connected to a syringe. In one or more embodiments as shown in FIG. 1, the bottom wall 531 of the scrubbing device 530 includes a threaded post 532 disposed in the center of the bottom wall 531 adjoining the common dividing wall 560 that corresponds to the internal thread 520 of the locking luer-type collar 519 on the distal end of the syringe barrel 511.

The scrubbing device 530 can achieve disinfection when used on needle-free connector ("NFC") by integrating a first disinfectant 547 in the first absorbent material 546 disposed and housed in the first chamber 545 of the first cup 540 and a second disinfectant 557 in the second absorbent material 556 disposed and housed in the second chamber 555 of the cup 550. The first disinfectant and second disinfectant (547, 557) can be directly included in the first chamber 545 and second chamber 555 and can be absorbed into first absorbent material 546 and into second absorbent material 556 (e.g. sponges or foam material) that fills the chamber of first cup 540 and second cup 550 respectively. The scrubbing device 530 is designed to be compatible in interacting with various disinfectants. In one or more embodiments, the first disinfectant 547 or second disinfectant 557 may include variations of alcohol or chlorhexidine. In one or more embodiments, the first disinfectant 547 or second disinfectant 557 is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the first disinfectant 547 or second disinfectant 557 comprises at least one of chlorhexidine gluconate and chlorhexidine diacetate. In one or more embodiments, the first disinfectant 547 or second disinfectant 557 is a fluid or a gel.

Figure 26:
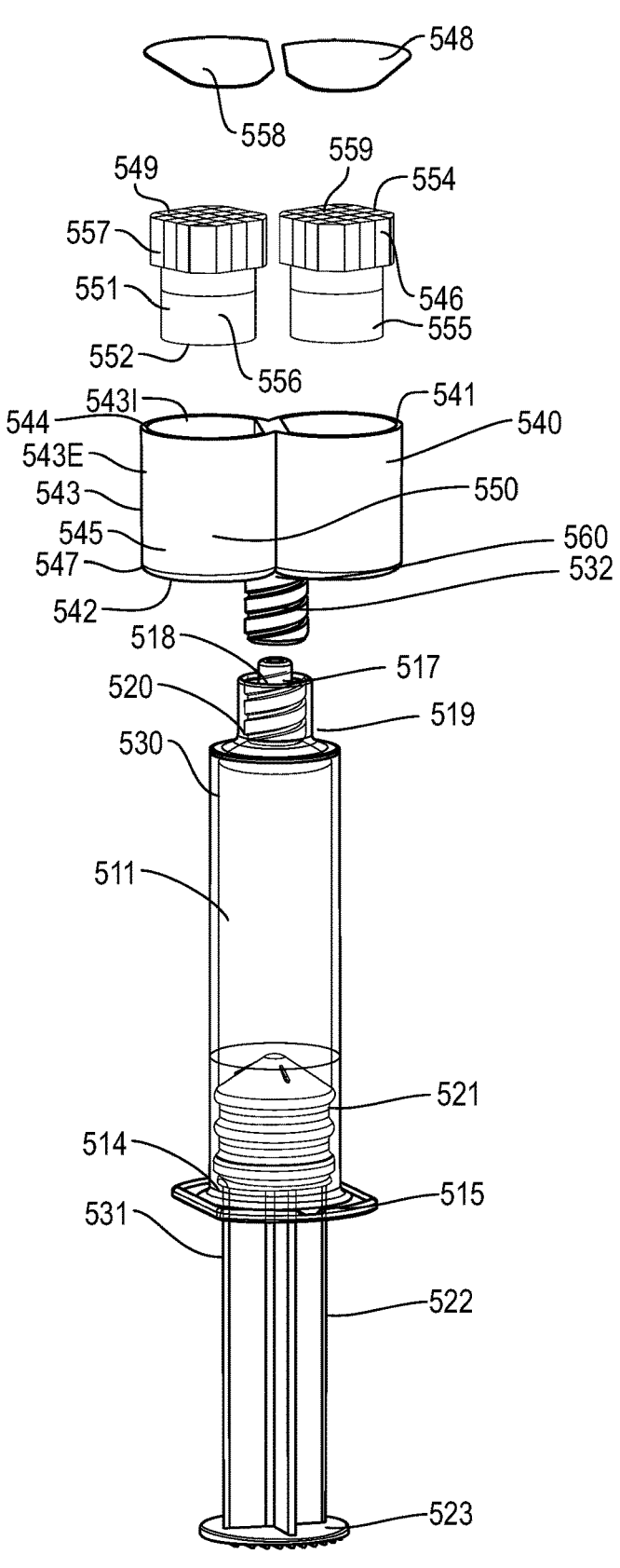
FIG. 26 illustrates an exploded perspective view of a disinfection unit 500 according to an exemplary fifth embodiment of the disclosure.
Figure 27:
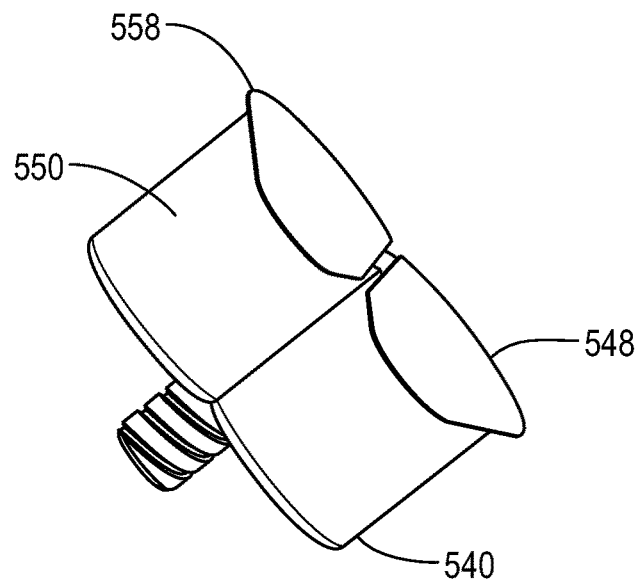
FIG. 27 illustrates a perspective side view of a scrubbing element according to an exemplary fifth embodiment of the disclosure.
Figure 28:
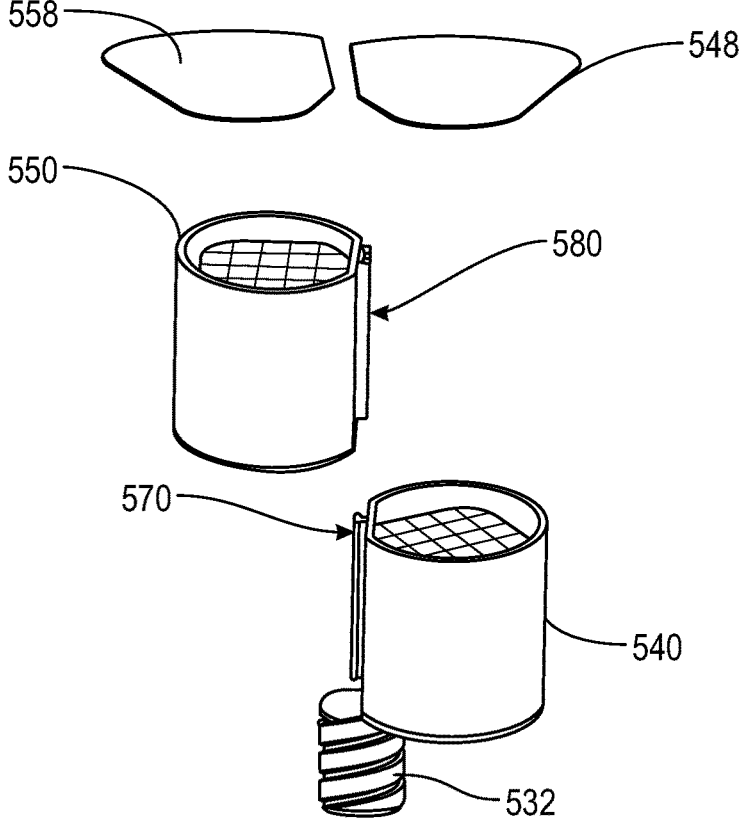
FIG. 28 illustrates a perspective view of the scrubbing element with the second cup detached from the first cup in accordance with an exemplary fifth embodiment of the disclosure.
Figure 29:
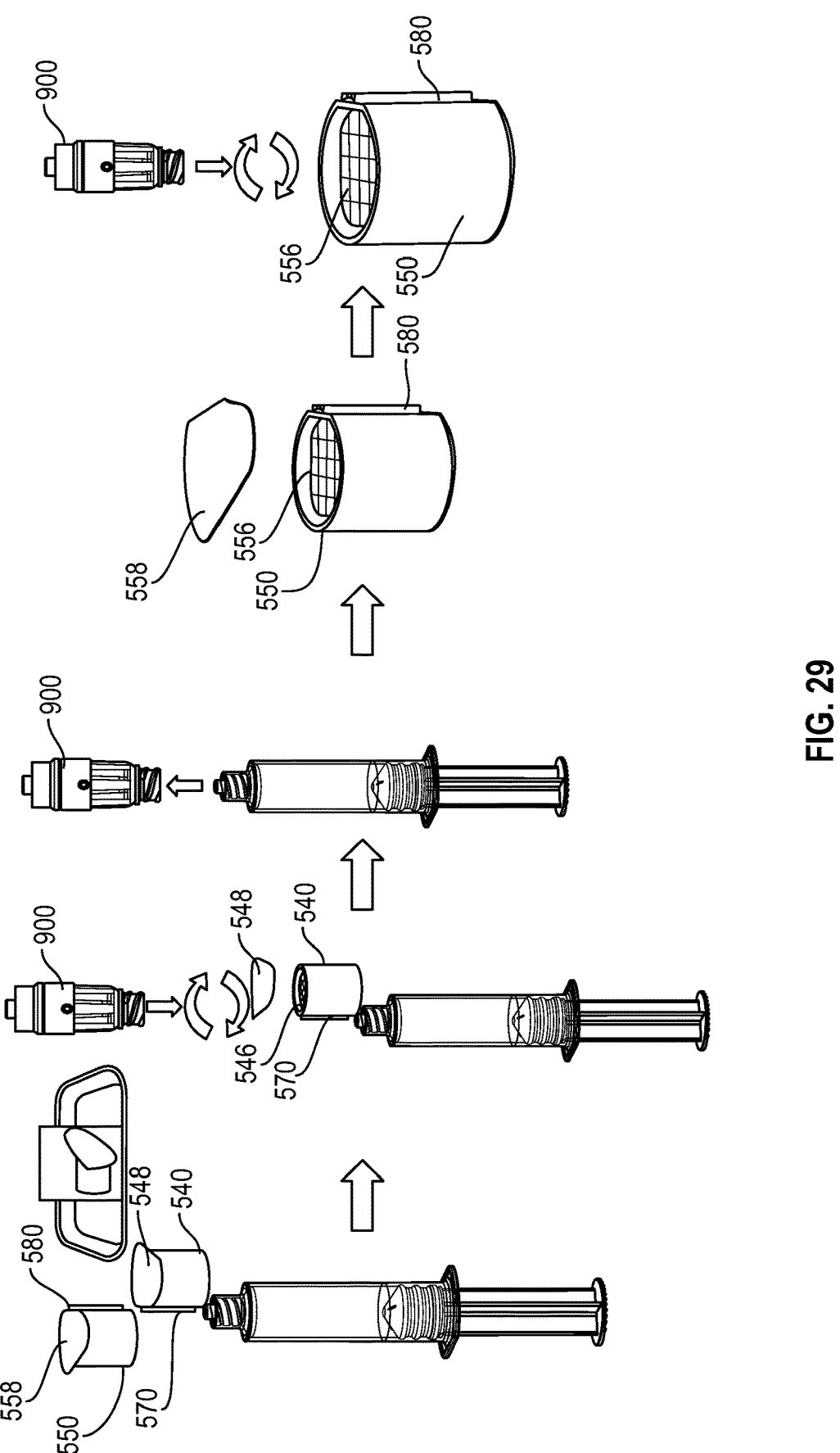
FIG. 29 illustrates a flow chart of a disinfection process using a disinfection unit 500 in accordance with an exemplary fifth embodiment of the disclosure.

First absorbent material 546 soaks up the first disinfectant 547 that is housed within the chamber 545 of the first cup 540. In one or more embodiments, the first absorbent material 546 is a nonwoven material, foam, or a sponge. In a specific embodiment, the foam is a polyurethane foam. In a specific embodiment the second absorbent material 556 is in the form of a foam plug. In one or more embodiments, the second absorbent material 556 includes one or more slits as shown in FIGS. 26 and 28.

A first peelable seal 548 having a top web 49 is disposed on the engagement surface of first cup 540 to prevent the first absorbent material 546 from exiting the chamber 545. With the first absorbent material 546 properly inserted into the chamber 545 of the first cup 540, the first peelable seal 548 may be secured to the engagement surface of the open end 544 of first cup 540 to seal the scrubbing device 530.

Second absorbent material 556 is disposed and housed in the chamber 555 of the second cup 550 and soaks up the second disinfectant 557 that is housed within the chamber 555 of the second cup 550. In one or more embodiments, the second absorbent material 556 is a nonwoven material, foam, or a sponge. In a specific embodiment, the foam is a polyurethane foam. In a specific embodiment the second absorbent material 556 is in the form of a foam plug. In one or more embodiments, the second absorbent material 556 includes one or more slits as shown in FIGS. 26 and 28.

A second peelable seal 558 having a top web 559 is disposed on the engagement surface of second cup 550 to prevent the second absorbent material 556 from exiting the chamber 555. With the second absorbent material 556 properly inserted into the chamber 555 of the second cup 550, the second peelable seal 558 may be secured to the engagement surface of the open end 554 of second cup 550 to seal the scrubbing device 530.

The first peelable seal 548 and second peelable seal 558 minimize entry of potential particulate hazard and also provides a substantially impermeable enclosure for the scrubbing device 530, provides a leak prevention and protection enclosure, protects the contents of first absorbent material 546 and second absorbent material 556 contained within the first chamber 545 and second chamber 555, respectively and/or maintains a sealed, sterilized environment. The first peelable seal 548 and second peelable seal 558 provides a sufficient seal at a range of temperatures, pressures, and humidity levels. Referring to FIG. 1, first peelable seal 548 and second peelable seal 558 may be disposed on the respective open ends (544, 554) of the first cup 540 and second cup 550 to prevent the pre-filled first disinfectant and second disinfectant (547, 557) from exiting the chamber of the respective first cup 540 and second cup 550.

The first peelable seal 548 and second peelable seal 558 can be a plastic sealed aluminum, and can be chemically-resistant, light-blocking, non-permeable, or sterile In one or more embodiments, the first peelable seal 548 and second peelable seal 558 comprises an aluminum or multi-layer polymer film peel back top. In a specific embodiment, the first peelable seal 548 and second peelable seal 558 is heat-sealed or induction sealed to the engagement surface of the open end (544, 554) of cup (540,550) to seal the scrubbing device 530. In one or more embodiments, the first peelable seal 548 and second peelable seal 558 comprises a moisture barrier.

The first absorbent material 546 and second absorbent material 556 and the disinfectant contacts the male luer connector, the female luer connector, and the hemodialysis connector after insertion of the connector into the open end (544, 554) of the respective cups 540 and 550.

In one or more embodiments, the female connector may be selected from the group consisting essentially of needle-free connectors, catheter luer connectors, stopcocks, and hemodialysis connectors. In one or more embodiments, the male connector may be an intravenous tubing end, a stopcock or male lock luer.

The first cup 540 and the second cup 550 are made from any type of plastic materials such as polycarbonate, polypropylene, polyethylene, polyethylene terephthalate, polylactide, acrylonitrile butadiene styrene or any other moldable plastic material used in medical devices. In one or more embodiments, the first cup 540 and the second cup 550 comprises a polypropylene or polyethylene material.

To avoid having to use different types of disinfecting caps to clean different types of connectors, disinfection device 500 with first cup 540 and second cup 550 is compatible and engages with male luer connectors and also with female luer connectors thereby allowing the user to clean different types of connectors with a single device. Upon mounting the first cup 540 and second cup 550 onto female luer connectors, or a male luer connector, the female or male medical connector engage the interior wall upon insertion into the chambers 545 or 555 and contact the first absorbent material 546 and into second absorbent material 556 soaked with disinfectant. Hence, the device of the present disclosure can disinfect both male and female luer connectors, thus fulfilling a current need in the art.

Other aspects of the present disclosure are directed to methods of disinfecting medical connectors and assemblies. In one or more embodiments, a method of disinfecting a medical connector comprises connecting the device of one or more embodiments to a medical connector, wherein connecting includes frictionally engaging the interior wall surface upon insertion into the chamber such that the medical connector contacts the absorbent material and the disinfectant.

In use, a clinician removes the first cup from the second cup of the scrubbing device and the clinician places the first cup 540 on a sterile tray for subsequent use of the sealed first cup for disinfection of needle-free connector ("NFC") before flushing. The clinician then peels the top web 559 of the second peelable seal 558 from the second cup 550 before flushing an IV line. The clinician then disinfects the NFC using the second cup 550. Upon insertion of the NFC into the second cup 550, the second absorbent material 556 soaked with second disinfectant 557 contacts the NFC. In one or more embodiments the NFC may be a male luer connector, the female luer connector, or the hemodialysis connector. Next, the clinician removes the second cup 550 of scrubbing device 530 from the syringe barrel, by applying a torque on the entire assembly thus unthreading second cup 550 of scrubbing device 530 from the locking luer-type collar 519 at the distal end of syringe barrel 511 to allow attachment of the flush syringe to the IV catheter line to flush the IV line. The clinician engages threads of the luer lock collar on the distal end of the syringe barrel to the NFC to connect the NFC to the flush syringe. The clinician then proceeds with flushing the IV line. Next, the clinician picks up detached first cup 540 of the scrubbing device 530 and peels top web 549 from first cup 540 after flushing IV line to expose the first absorbent material 546 soaked in the first disinfectant 547 and disinfects the NFC using the first cup 540 in which the first absorbent material 546 soaked in the first disinfectant 547 in the first cup 540 contacts the male luer connector, the female luer connector, and the hemodialysis connector after insertion of the NFC connector into first cup 540. As in current practice, the clinician then administers medicine and performs a second flush of the IV line using a Flush syringe to remove any medication left in your catheter and scrubs the hub using a disinfecting wipe or scrubbing device. The clinician then "locks" the IV line using a lock syringe filled with a heparin flush to help prevent blood clots from forming in the catheter. Finally, a new disinfecting cap is attached to the dwelling catheter hub.

As noted above, currently products and SASH practice does not address any cleaning after the initial flushing process as the sanitization ends after the first flush. The benefit of the embodiments of the present invention which includes the two individually packaged first cup 540 and second cup 550 both having disinfectant-loaded absorbent materials (546,556) is institution of a two-step sanitization that provides additional protection to the patient by including an additional cleaning step using the IPA or scrubbing device to sanitize the hub or connecting interface prior to medication or lock solution administration thereby further preventing potential infections to the patient.

When using the first cup 540, compression of the first absorbent material 546 toward the closed end 542 of the chamber 545 upon connection to the female luer connector or the male luer connector allows the connector to contact the first disinfectant 547 to disinfect the female luer connector or the male luer connector. Similarly, when using the second cup 550, compression of the second absorbent material 556 toward the closed end 552 of the chamber 555 upon connection to the female luer connector or the male luer connector allows the connector to contact the second disinfectant 557 to disinfect the female luer connector or the male luer connector.

In one or more embodiments, an assembly comprises the device of one or more embodiments connected to a medical connector. In one or more embodiments, the medical con-nector is selected from a male luer connector, a female luer connector, and needleless connector.

Figure 30:
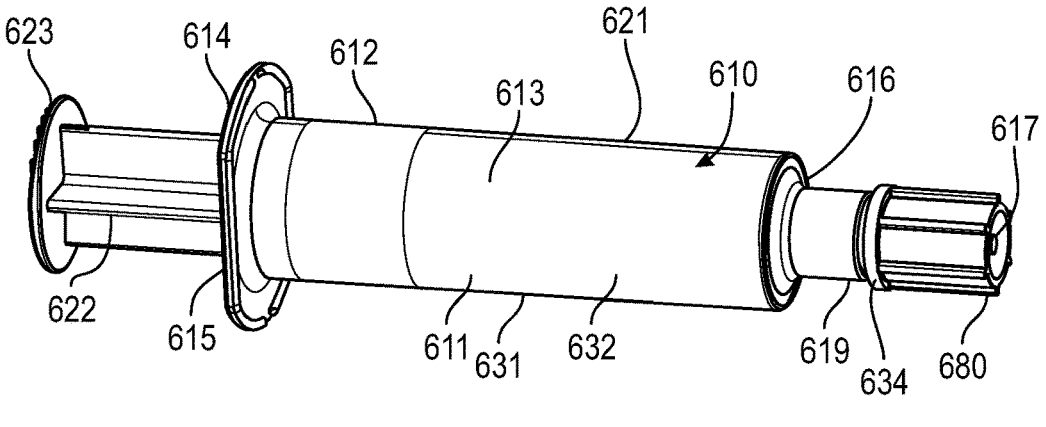
FIG. 30 illustrates a perspective view of a disinfection unit 600 according to an exemplary sixth embodiment of the disclosure.

In another alternate embodiment, referring to FIG. 30, a disinfection unit 600 includes a flush syringe assembly 610 having a syringe barrel 611 having an elongate body 612 defining a chamber 613 for retaining fluid. The syringe barrel 611 includes an open proximal end 614 having a flange 615 and a distal end 616 including a tip 617 having a passageway 518 therethrough in fluid communication with the chamber. The distal end 616 of the barrel also includes a locking luer-type collar 619 concentrically surrounding tip 617. The locking luer-type collar 619 has an internal thread. Syringe assembly 610 further includes a stopper 621 con-nected to an elongate plunger rod 622 having a thumb press 623 at its proximal end. A tip cap 680 is threaded onto the distal end of the barrel to provide closure integrity for the syringe contents through the shelf life and is removed by the user prior to flush administration. Syringe assembly 620 further includes a stopper 631 connected to an elongate plunger rod 632 having a flange 634 at its proximal end.

Two individually packaged disinfectant-loaded scrubbing pads (650, 660) are attached to the flange 615 of the syringe barrel 611 with a detachable loop of string 640, the string 640 being attached to the flange by an adhesive or threaded onto a small hole 670 disposed on the flange 615. Each end of the string 640 being attached to one of the two individu-ally packaged disinfectant-loaded scrubbing pads (650, 660). The flange 615 can have one or more notches or holes to which for a loop of string is attached to each end of the string attached separately to the two individually packaged disinfectant-loaded scrubbing pads (650, 660). Still further, the string may be wrapped around a groove, notch or hole in the flange for easy gripping of the two individually packaged disinfectant-loaded scrubbing pads (650, 660) by the user. The two individually packaged disinfectant-loaded scrub-bing pads (650, 660) provided enforce the solution of sanitization that may not be followed otherwise and provides additional protection to the patient by including an addi-tional cleaning step using the IPA or scrubbing device to sanitize the hub or connecting interface prior to medication or lock solution administration thereby further preventing potential infections to the patient.

In use, the catheter that the flush syringe will be connected to needs to be disinfected with one of the two individually packaged disinfectant-loaded scrubbing pads (650, 660). In use, a clinician removes the first of the two individually packaged disinfectant-loaded scrubbing pad (650) and the clinician places the first individually packaged disinfectant-loaded scrubbing pad (650) on a sterile tray for subsequent use before flushing. The clinician then opens individually packaged disinfectant-loaded scrubbing pad (650) before flushing an IV line. The clinician then disinfects the NFC using the individually packaged disinfectant-loaded scrub-bing pad (650) by contacting the NFC with the into the individually packaged disinfectant-loaded scrubbing pad (650). In one or more embodiments the NFC may be a male luer connector, the female luer connector, or the hemodi-alysis connector. Next, the clinician engages threads of the luer lock collar on the distal end of the syringe barrel to the NFC to connect the NFC to the flush syringe. The clinician then proceeds with flushing the IV line. Next, the clinician opens the individually packaged disinfectant-loaded scrub-bing pad (660) and contacts the male luer connector, the female luer connector, and the hemodialysis connector.

As noted above, currently products and SASH practice does not address any cleaning after the initial flushing process as the sanitization ends after the first flush. The benefit of the embodiments of the present invention which includes the two individually packaged disinfectant-loaded scrubbing pads (650, 660) is institution of a two-step sani-tization that provides additional protection to the patient by including an additional cleaning step using the IPA or scrubbing device to sanitize the hub or connecting interface prior to medication or lock solution administration thereby further preventing potential infections to the patient.

Figure 31:
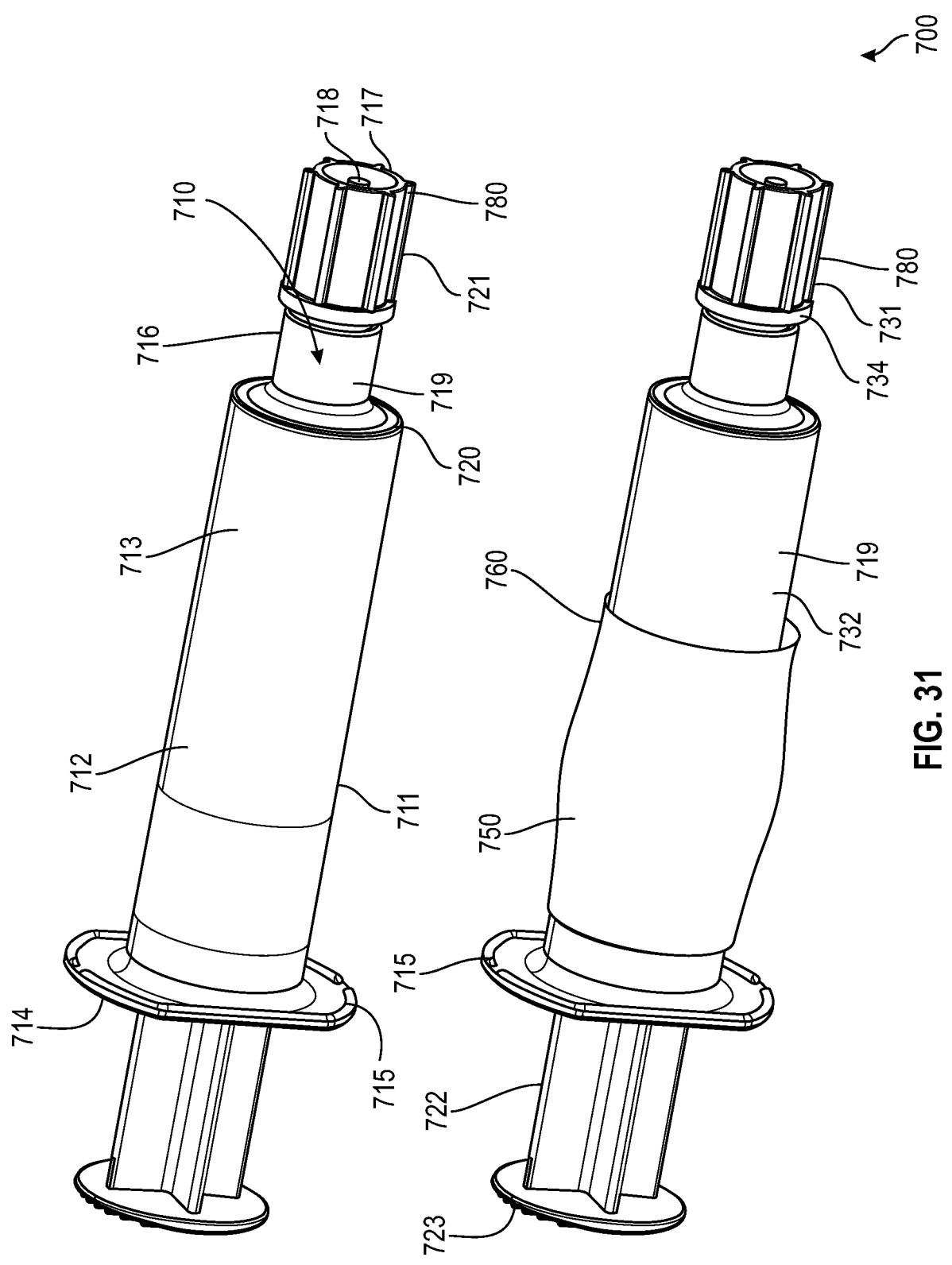
FIG. 31 illustrates a perspective view of a disinfection unit 700 according to an exemplary seventh embodiment of the disclosure.

In another alternate embodiment, referring to FIG. 31, a disinfection unit 700 includes a flush syringe assembly 710 having a syringe barrel 711 having an elongate body 712 defining a chamber 713 for retaining fluid. The syringe barrel 711 includes an open proximal end 714 having a flange 715 and a distal end 716 including a tip 717 having a passageway 718 therethrough in fluid communication with the chamber. The distal end 716 of the barrel also includes a locking luer-type collar 719 concentrically surrounding tip 717. The locking luer-type collar 719 has an internal thread 720. Syringe assembly 710 further includes a stopper 721 connected to an elongate plunger rod 722 having a thumb press 723 at its proximal end. A tip cap 780 is threaded onto the distal end of the barrel to provide closure integrity for the syringe contents through the shelf life and is removed by the user prior to flush administration. Syringe assembly 710 further includes a stopper 731 connected to an elongate plunger rod 732 having a flange 734 at its proximal end.

Two individually packaged disinfectant-loaded scrubbing pads (750, 760) are attached to the elongate body 712 of the syringe barrel 710 using an adhesive or external plastic wrap. The two individually packaged disinfectant-loaded scrubbing pads (750, 760) provided enforce the solution of sanitization that may not be followed otherwise and provides additional protection to the patient by including an addi-tional cleaning step using the IPA or scrubbing device to sanitize the hub or connecting interface prior to medication or lock solution administration thereby further preventing potential infections to the patient. The syringe assembly 710 can be a pre-filled syringe assembly. It can be appreciated that the two disinfectant-loaded scrubbing pads (750, 760) can be joined or connected together by a frangible or perforated portion for ease of removal from the syringe barrel or syringe assembly. In an alternate embodiment, the two individual disinfectant-loaded scrubbing pads (750, 760) may be adhered to the syringe barrel using a shrink-wrap type label which can encompass a portion of the barrel until the practitioner is ready to use the syringe assembly.

The catheter that the flush syringe will be connected to needs to be disinfected with one of the two individually packaged disinfectant-loaded scrubbing pads (650, 660). In use, a clinician removes the first of the two individually packaged disinfectant-loaded scrubbing pad (750) from the elongate body 712 of the syringe barrel 710 and the clinician places the first individually packaged disinfectant-loaded scrubbing pad (750) on a sterile tray for subsequent use before flushing. The clinician then removes the second of the two individually packaged disinfectant-loaded scrubbing pad (760) from the elongate body 712 of the syringe barrel 710 and opens individually packaged disinfectant-loaded scrubbing pad (760) before flushing an IV line. The clinician then disinfects the needle-free connector ("NFC") using the individually packaged disinfectant-loaded scrubbing pad (760) by contacting the NFC with the disinfectant-loaded scrubbing pad (760). In one or more embodiments the NFC may be a male luer connector, the female luer connector, or the hemodialysis connector. Next, the clinician engages threads of the luer lock collar on the distal end of the syringe barrel to the NFC to connect the NFC to the flush syringe. The clinician then proceeds with flushing the IV line. Next, the clinician opens the first individually packaged disinfectant-loaded scrubbing pad (750) and contacts the male luer connector, the female luer connector, and the hemodialysis connector.

As noted above, currently products and SASH practice does not address any cleaning after the initial flushing process as the sanitization ends after the first flush. The benefit of the embodiments of the present invention which includes the two individually packaged disinfectant-loaded scrubbing pads (750, 760) is institution of a two-step sanitization that provides additional protection to the patient by including an additional cleaning step using the IPA or scrubbing device to sanitize the hub or connecting interface prior to medication or lock solution administration thereby further preventing potential infections to the patient.

While the present disclosure has been shown and described with reference to certain exemplary embodiments thereof, it will be understood by those skilled in the art that various changes in form and details may be made therein without departing from the spirit and scope of the embodiments of the present disclosure. Also, the inner and/or the outer housing of the cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant field of invention.

Other objects, advantages and salient features of the disclosure will become apparent to those skilled in the art from the details provided, which, taken in conjunction with the annexed drawing figures, disclose exemplary embodiments of the disclosure.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A disinfection device comprising:
a scrubbing device having a first cup, a second cup, and a bottom wall spanning an entirety of the first cup and the second cup, wherein the first cup and the second cup are bounded by a dividing wall,
the first cup including a first integral body, a first closed end, a first annular wall having a length LC extending from the first closed end to a first open end and defining a first chamber containing a first absorbent material and a first disinfectant, the first open end having a peripheral ledge extending radially inward from the first open end defining an end face and an engagement surface;
a first peelable seal disposed on the end face of the first cup to prevent the first disinfectant from exiting the first chamber;
a connection element is disposed on the bottom wall of the first cup of the scrubbing device, wherein the connection element is a threaded post;
the second cup including a second integral body, a second closed end, a second annular wall having a length LC extending from the second closed end to a second open end and defining a second chamber containing a second absorbent material and a second disinfectant, the second open end having a peripheral ledge extending radially inward from the second open end defining a second end face and a second engagement surface; and
a second peelable seal disposed on the second end face of the second cup to prevent the second disinfectant from exiting the second chamber.

2. The disinfection device of claim 1, wherein the connection element is a luer lock collar.

3. The disinfection device of claim 1, wherein the threaded post mates with a luer lock collar of a flush syringe.

4. The disinfection device of claim 1, wherein the peripheral ledge is sized and adapted to receive a thumb press of a plunger rod.

5. The disinfection device of claim 1, wherein the first cup and the second cup comprise a polypropylene or polyethylene material.

6. The disinfection device of claim 1, wherein the first absorbent material and second absorbent material is a foam.

7. The disinfection device of claim 6, wherein the first absorbent material and second absorbent material is a polyurethane foam.

8. The disinfection device of claim 1, wherein the first absorbent material and second absorbent material is a sponge.

9. The disinfection device of claim 1, wherein the first absorbent material and second absorbent material has slits.

10. The disinfection device of claim 1, wherein a compression of the first absorbent material and second absorbent material toward the first closed end of the first chamber and second chamber occurs upon connection to a medical connector.

11. The disinfection device of claim 10, wherein contact with the first absorbent material and second absorbent material disinfects the medical connector.

12. The disinfection device of claim 1, wherein the first disinfectant and second disinfectant is selected from a group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof.

13. The disinfection device of claim 12, wherein the first disinfectant and second disinfectant comprises at least one of chlorhexidine gluconate and chlorhexidine diacetate.

14. The disinfection device of claim 12, wherein the first disinfectant and second disinfectant is a fluid or a gel.

15. The disinfection device of claim 1, wherein the first peelable seal and second peelable seal comprises an aluminum or multi-layer polymer film peel back top.

16. The disinfection device of claim 1, wherein the first peelable seal and second peelable seal is heat-sealed or induction sealed to the engagement surface.

17. The disinfection device of claim 1, wherein the threaded post is disposed in the center of the bottom wall of the scrubbing device, adjoining the dividing wall.

18. An assembly comprising:

a disinfection unit of claim 1 connected with a syringe assembly including a syringe barrel having an elongate body defining a chamber, an open proximal end having a flange and a distal end having a tip having a passageway therethrough in fluid communication with the chamber, a stopper connected to an elongate plunger rod having a thumb press at its proximal end, and a locking luer-type collar on the distal end of the syringe barrel;

the first cup connected to the locking luer-type collar on the distal end of the syringe barrel; and the second cup of the scrubbing device is snap fit to the thumb press of the elongate plunger rod of the syringe assembly.

19. A method of disinfecting a medical connector comprising:

connecting the assembly of claim 18 to a medical connector, wherein connecting includes removing the second cup from the syringe assembly, peeling a top web of the first peelable seal from the first cup;

inserting a NFC into the chamber of the first cup and contacting the NFC with the first absorbent material soaked with a first disinfectant;

removing first cup of the scrubbing device from the syringe barrel by applying a torque on the assembly thus unthreading first cup from the locking luer-type collar at the distal end of barrel;

attaching a flush syringe to an IV catheter line by engages threads of the luer lock collar on the distal end of the syringe barrel to connect the NFC to the flush syringe and flushing the IV catheter line;

unthreading the flush syringe from the NFC and peeling the top web from the second cup to expose the second absorbent material soaked in the second disinfectant; and inserting the NFC into the chamber of the second cup and contacting the NFC with the first absorbent material soaked with the first disinfectant.

* * * * *